US006335427B1

(12) United States Patent
Mynott et al.

(10) Patent No.: US 6,335,427 B1
(45) Date of Patent: Jan. 1, 2002

(54) COMPONENT OF STEM BROMELAIN

(75) Inventors: Tracey Lehanne Mynott; Christian Engwerda, both of Richmond; Keith Peek, Ewloe, all of (GB)

(73) Assignee: Provalis UK Limited, Flintshire (GB)

( * ) Notice: Subject to any disclaimer, the term of this patent is extended or adjusted under 35 U.S.C. 154(b) by 0 days.

(21) Appl. No.: 09/382,689

(22) Filed: Aug. 25, 1999

Related U.S. Application Data

(63) Continuation of application No. PCT/GB98/00592, filed on Feb. 25, 1998.

(30) Foreign Application Priority Data

| Feb. 25, 1997 | (GB) | 9703827 |
| Feb. 25, 1997 | (GB) | 9703850 |
| Feb. 28, 1997 | (GB) | 9704252 |

(51) Int. Cl.$^7$ .................................................. A61K 35/78
(52) U.S. Cl. ..................... 530/379; 530/350; 530/370; 530/412; 514/2
(58) Field of Search .................. 530/350, 370, 530/379, 412; 514/2

(56) References Cited

U.S. PATENT DOCUMENTS

| 5,223,406 A | 6/1993 | Ransberger et al. ........ 435/68.1 |
| 5,387,517 A | 2/1995 | Cini .............................. 435/212 |

FOREIGN PATENT DOCUMENTS

| DE | 43 02 060 A1 | 7/1994 |
| EP | 0 313 346 A2 | 4/1989 |
| WO | WO 88/01506 A1 | 3/1988 |
| WO | WO 93/01800 | 2/1993 |
| WO | WO 94/00147 A1 | 1/1994 |
| WO | WO 95/00169 A1 | 1/1995 |
| WO | WO 96/00082 A1 | 1/1996 |
| WO | WO 97/24138 A2 | 7/1997 |
| WO | WO 98/38291 A1 | 9/1998 |
| WO | WO 99/00141 | 1/1999 |
| WO | WO 00/14253 | 3/2000 |

OTHER PUBLICATIONS

Avruch, J., et al., "Raf meets Ras: completing the framework of a signal transduction pathway," *TIBS* 19:279–283 (1994).
Belham, C.M., et al., "Trypsin stimulates proteinase–activated receptor–2–dependent and –independent activation of mitogen–activated protein kinases," *Biochem J.* 320:939–946 (1996).
Bliska, J.B., et al., "Signal Transduction in the Mammalian Cell during Bacterial Attachment and Entry," *Cell* 73:903–920 (1993).
Cantrell, D., "T Cell Antigen Receptor Signal Transduction Pathways," *Annu. Rev. Immunol.* 14:259–274 (1996).
Fang, F.C., "NO Contest: Nitric Oxide Plays Complex Roles in Infection," *ASM News* 63:668–673 (1997).
Filippova, I.Y., et al., "L–Pyroglutamyl–L–phenylalanyl–L–leucine–p–nitroanilide—A Chromogenic Substrate for Thiol Proteinase Assay," *Anal. Biochem.* 143:293–297 (1984).
Fox, B.S., "Antigen presenting cell–derived co–stimulatory signals can selectively regulate IL–2 and IL–4 production from a $T_hO$ cell hybridoma," *Intl. Immunol.* 5:323–330 (1993).
Galán, J.E., et al., "Involvement of the epidermal growth factor receptor in the invasion of cultured mammalian cells by *Salmonella typhimurium*," *Nature* 357:588–589 (1992).
Garbin, F., et al., "Bromelain proteinase F9 augments human lymphocyte–mediated growth inhibition of various tumor cells in vitro," *Intl. J. Oncol.* 5:197–203 (1994).
Gillis, S., et al., T Cell Growth Factor: Parameters of Production and a Quantitative Microassay for Activity, *J. Immunol.* 120:2027–2032 (1978).
Harrach, T., et al., "Isolation and Partial Characterization of Basic Proteinases from Stem Bromelain," *J. Protein Chem.* 14:41–52 (1995).
Hibbs, Jr., J.B., Synthesis of nitric oxide from L–arginine: a recently discovered pathway induced by cytokines with antitumor and antimicrobial activity, *Res. Immunol.* 142:565–569 (1991).
Izquierdo, M., et al., "Role of Protein Kinase C in T–Cell Antigen Receptor Regulation of $p21^{ras}$: Evidence that Two $p21^{ras}$ Regulatory Pathways Coexist in T Cells," *Mol. Cell. Biol.* 12:3305–3312 (1992).
Izquierdo, M., et al., "$p21^{ras}$ Couples the T Cell Antigen Receptor to Extracellular Signal–regulated Kinase 2 in T Lymphocytes," *J. Exp. Med.* 178:1199–1208 (1993).
June, C.H., et al., "Increases in Tyrosine Phosphorylation are Detectable Before Phospholipase C Activation After T Cell Receptor Stimulation," *J. Immunol.* 144:1591–1599 (1990).
June, C.H., et al., "Inhibition of tyrosine phosphorylation prevents T–cell receptor–mediated signal transduction," *Proc. Natl. Acad. Sci. USA* 87:7722–7726 (1990).
Kaye, P.M., and Bancroft, G.J., "*Leishmania donovani* Infection in scid Mice: Lack of Tissue Response and In Vivo Macrophage Activation Correlates with Failure to Trigger Natural Killer Cell–Derived Gamma Interferon Production In Vitro," *Infection and Immunity* 60:4335–4342 (1992).
Kelland, L.R., et al., "Preclinical Antitumor Evaluation of Bis–acetato–ammine–dichloro–cyclohexylamine Platinum(IV): an Orally Active Platinum Drug," *Cancer Res.* 53:2581–2586 (1993).
Lowry, O.H., et al., "Protein Measurement with the Folin Phenol Reagent," *J. Biol. Chem.* 193:265–275 (1951).

(List continued on next page.)

*Primary Examiner*—Jeffrey Stucker
(74) *Attorney, Agent, or Firm*—Sterne, Kessler, Goldstein & Fox, P.L.L.C.

(57) ABSTRACT

A novel protein is a component of stem bromelain and is an anti-cancer agent, an immunostimulant and has antimicrobial activity. The protein may be isolated from stem bromelain by methods such as HPLC and has a molecular weight of about 25.08 kDa and an isoelectric point of about 3.8 or 3.85.

7 Claims, 18 Drawing Sheets

OTHER PUBLICATIONS

Maurer, H.R., et al., Bromelain Induces the Differentiation of Leukemic Cells in Vitros: An Explanation for its Cytostatic Effects? *Planta medica 54*:377–381 (1988).

Munzig, E., et al., "Bromelain protease F9 reduces the CD44 mediated adhesion of human peripheral blood lymphocytes to human umbilical vein endothelial cells," *FEBS Lett. 351*:215–218 (1994).

Napper, D.D., et al., "Purification and characterization of multiple forms of the pineapple–stem–derived cysteine proteinases ananain and comosain," *Biochem. J. 301*:727–735 (1994).

Ota, S., et al., "Reinvestigation of Fractionation and Some Properties of the Proteolytically Active Components of Stem and Fruit Bromelains," *J. Biochem. 98*:219–228 (1985).

Perandones, C.E., et al., "Regulation of Apoptosis In Vitro in Mature Murine Spleen T Cells," *J. Immunol. 151*:3521–3529 (1993).

Rayter, S.I., et al., "$p21^{ras}$ mediates control of IL–2 gene promoter function in T cell activation," *EMBO J. 11*:4549–4556 (1992).

Roach, T.I.A., et al., "Role of inorganic Nitrogen Oxides and Tumor Necrosis Factor Alpha in Killing *Leishmania donovani* Amastigotes in Gamma Interferon–Lipopolysaccharide–Activated Macrophages from $Lsh^s$ and $Lsh^r$ Congenic Mouse Strains," *Infection and Immunity 59*:3935–3944 (1991).

Rowan, A.D., et al., "Ananain: A Novel Cysteine Proteinase Found in Pineapple Stem," *Arch. Biochem. Biophys. 267*:262–270 (1988).

Rowan, A.D., and Buttle, D.J., "Pineapple Cysteine Endopeptidases," *Meth. Enzymol. 244*: 555–568 (1994).

Sager, S.M. et al., "Nitric oxide and anti–cancer therapy," *Cancer Treatment Rev. 21*:159–181 (1995).

Tussig, S.J., et al., "Inhibition of Tumor Growth in vitro by Bromelain, an Extract of the Pineapple Plant (*Ananas comosus*)," *Planta Medica 51*:538–539 (1985).

Truneh, A., et al., "Early steps of lymphocyte activation bypassed by synergy between calcium ionophores and phorbol ester," *Nature 313*:318–320 (1985).

Vouret–Craviari, V., et al., "Differential activation of $p44^{mapk}$ (ERK1) by α–thrombin and thrombin–receptor peptide agonist," *Biochem. J. 269*:209–214 (1993).

Derwent World Patent Index, Accession No. 1985–028979 [05], English language abstract for Document AL1, JP 59–225122.

Derwent World Patent Index, Accession No. 94–236002/199429, English language abstract for Document AL2, DE 4 302 060.

EMBL/GenBank/DDBJ Databases, Accession No. 023791, from Muta, E., et al., created Jan. 1, 1998.

EMBL/GenBank/DDBJ Databases, Accession No. 023801, from Muta, E., et al., created Jan. 1, 1998.

COMPONENT OF STEM BROMELAIN

CROSS REFERENCE TO RELATED APPLICATIONS

The present application is a continuation of International Application No. PCT/GB98/00592, filed Feb. 25, 1998.

BACKGROUND OF THE INVENTION

1. Field of the Invention

The present invention relates to a protein which is a component of bromelain. In particular, the invention relates to a protein which is responsible for the anti-cancer activity of bromelain and which also has activity as an immunostimulant, and an antimicrobial agent.

2. Related Art

Bromelain is the collective name for the proteolytic enzymes found in the tissues of the plant Bromeliaceae. Although fruit bromelain is known, the most common form of bromelain is a mixture of various moieties derived from the stem of the pineapple plant (*Ananas comosus*). Stem bromelain (hereafter called bromelain) is known to contain at least five proteolytic enzymes but also non-proteolytic enzymes, including an acid phosphatase and a peroxidase; it may also contain amylase and cellulase activity. In addition, various other components are present.

Bromelain has previously been used in the treatment of a variety of conditions including inflammation and, in particular, it has been used in the treatment of diarrhoea. The use of bromelain in the treatment of infectious diarrhoea is described in WO-A-9301800, where it is suggested that bromelain works by destroying intestinal receptors for pathogens by proteolysis, and in WO-A-8801506, which teaches that bromelain detaches pathogens from intestinal receptors.

Taussig et al, *Planta Medica*, 1985, 538–539 and Maurer et al, *Planta Medica*, 1988, 377–381 both suggest that bromelain may be of use in inhibiting tumour growth. U.S. Pat. No. 5,223,406, DE-A-4302060 and JP-A-59225122 also teach the use of bromelain in the treatment of cancer. U.S. Pat. No. 5,223,406 teaches that bromelain is capable of inducing tumour necrosis factor (TNF) while DE-A4302060 teaches that bromelain can prevent metastasis by the structural modification of the tumour surface protein CD44.

In WO-A-9400147, various experiments were described which demonstrate that proteolytic enzymes and, in particular, bromelain, are capable of inhibiting secretion. The application also discloses that bromelain can reduce toxin binding activity and can inhibit the secretory effect of toxins such as heat labile toxin (LT) and cholera toxin (CT) and also toxins such as heat stable toxin (ST). These observations were explained by the fact that one component of the bromelain mixture, stem bromelain protease, appears to be capable of modulating cyclic nucleotide pathways and this is discussed further in WO-A-9500169. In addition, bromelain has also been demonstrated to inhibit secretion caused by the calcium dependent pathway.

WO-A-9600082 also relates to bromelain and discloses that crude bromelain is capable of interfering with signalling pathways which are important for growth, in particular, signalling pathways which lead to the production of growth factors such as interleukin-2 (IL-2), platelet derived growth factor (PDGF) and insulin like growth factor (IGF). This document teaches that, as a consequence of its ability to block signalling pathways, bromelain is capable of acting as an anti-cancer agent. In addition, bromelain can be used either as an immunosuppressive agent or an immunostimulant depending on the type of cell being treated and whether the cell has previously been activated.

From the prior art, it is clear that bromelain is a mixture which has a variety of different physiological effects. Not all of the components of the bromelain mixture have been characterised and so, except for stem bromelain protease, whose activity we have described, it is not clear which of the components is responsible for which of the various different effects of bromelain. This is, of course, a major disadvantage if the bromelain mixture is to be administered as a pharmaceutical because while one component of bromelain might give the desired effect, there may well be unwanted side effects arising from the action of some other component of the bromelain mixture.

SUMMARY OF THE INVENTION

It would therefore be beneficial if individual components of bromelain giving rise to particular medicinal activities could be isolated and administered separately so as to lessen the possibility of side effects.

The present inventors have now isolated, purified and characterised one such component of bromelain which is distinct from other known components of the mixture and which has been found to have anti-cancer activity.

DETAILED DESCRIPTION OF THE INVENTION

In a first aspect of the present invention there is provided a protein which is a component of bromelain, has a molecular weight of about 22.2 to 25.08 kDa as determined by SDS-PAGE, has an isoelectric point of 3.8 to 4.79 and has the amino terminal sequence:

Val Pro Gln Ser Ile Asp Trp Arg Asp Tyr Gly Ala Val Asn Glu Val Lys Asn (SEQ ID NO:1)

and, additionally, contains the following sequences:

Gly Gly Trp Glu Phe Lys (SEQ ID NO: 2)

Lys Ala Val Asn Gly (SEQ ID NO: 3)

Tyr Trp Ile Val Arg (SEQ ID NO: 4)

Asn Ser Trp Gly Ser Ser Trp Gly Glu Gly Gly Tyr Val Arg (SEQ ID NO:5)

Thr Ser Leu Asn His Ala Ile Thr Ile Ile Val Tyr (SEQ ID NO: 6)

Leu Pro Glu Phe (Gln) Pro (Gln) Val Leu Asp-Ala- (SEQ ID NO: 7)

Gly Val Ser Ser Ser Gly Ala Cys Gly Ile Ala Met Ser Pro Leu-Thr- (SEQ ID NO: 8)

Gly Gly Val Phe Ser Gly Pro Ala Gly (SEQ ID NO: 9)

Asn Asn Ala Tyr (SEQ ID NO: 10)

Ser Ser Gly Thr Lys Tyr Trp-Val- (SEQ ID NO: 11);

where the bracketed amino acids represent alternatives to the preceding amino acid and a "-" represents an unidentified amino acid.

The protein of the present invention (designated CCX2 by the inventors) is largely responsible for the anti-cancer activity of bromelain since other known components such as stem bromelain protease, ananain, comosain, and F9 have all been found to have reduced anti-cancer activity. Also, because it is a single molecule, the protein of the invention does not have the disadvantages of multi-component mixtures when used as a pharmaceutical agent.

The protein may be isolated from the bromelain mixture by conventional methods, for example by chromatography. High performance liquid chromatograpy (HPLC) is suitable for the purpose and particularly good separation of bromelain proteins may be achieved by fast protein liquid chromatography (FPLC™) using a column packing material such as SP-sepharose. As will be described in more detail in the examples, in chromatography on SP-sepharose using a linear gradient of 0 to 0.8M sodium chloride in acetate buffer over 300 ml, the protein of the present invention was contained in the fraction represented by the second sharp peak off the column. This fraction was designated the CCX fraction. The protein of the invention was the major component of the CCX fraction and was isolated from the minor components by conventional methods which will be described in greater detail below.

Therefore, in a second aspect of the invention, there is provided a protein which is a component of bromelain, has a molecular weight of about 22.2 to 25.08 kDa as determined by SDS-PAGE and is obtainable by the following method:

i. dissolving bromelain in acetate buffer at pH 5.0;

ii. separating the components of bromelain by fast flow high performance liquid chromatography on S-sepharose eluting with a linear gradient of 0 to 0.8 M sodium chloride in acetate buffer over 300 ml;

iii. collecting the fraction corresponding to the second sharp peak off the column; and iv. isolating the major protein from the fraction collected in (iii) by anion chromatography and hydrophobic interaction chromatography.

It is known from, for example, U.S. Pat. No. 5,223,406 and WO-A-9600082 that the bromelain mixture has anti cancer activity but it has previously been assumed that one of the known components of bromelain, probably stem bromelain protease, was responsible for this activity. It has now been found that this is not the case and that the protein of the present invention is an anti-cancer agent whereas stem bromelain protease has no anti-cancer activity.

The protein of the present invention has a high degree of homology with fruit bromelain protease, an enzyme isolated from fruit bromelain by Muta et al and submitted to the DDBJ/EMBL/GenBank databases on Aug. 28, 1997. The sequence identity is not complete, however and the two enzymes are, of course, derived from different sources. However, the high degree of homology between the proteins makes it likely that fruit bromelain protease will have similar anti-cancer activity to CCX2.

In a further aspect of the present invention there is provided fruit bromelain protease or an isolated and purified protein which is a component of bromelain, has a molecular weight of about 22.2 to 25.08 kDa as determined by SDS-PAGE, has an isoelectric point of 3.8 to 4.79 and has the amino terminal sequence:

Val Pro Gln Ser Ile Asp Trp Arg Asp Tyr Gly Ala Val Asn Glu Val Lys Asn (SEQ ID NO:1)

and, additionally, contains the following sequences:

Gly Gly Trp Glu Phe Lys (SEQ ID NO: 2)

Lys Ala Val Asn Gly (SEQ ID NO: 3)

Tyr Trp Ile Val Arg (SEQ ID NO: 4)

Asn Ser Trp Gly Ser Ser Trp Gly Glu Gly Gly Tyr Val Arg (SEQ ID NO:5)

Thr Ser Leu Asn His Ala Ile Thr Ile Ile Val Tyr (SEQ ID NO: 6)

Leu Pro Glu Phe (Gln) Pro (Gln) Val Leu Asp-Ala- (SEQ ID NO: 7)

Gly Val Ser Ser Ser Ser Gly Ala Cys Gly Ile Ala Met Ser Pro Leu-Thr- (SEQ ID NO: 8)

Gly Gly Val Phe Ser Gly Pro Ala Gly (SEQ ID NO: 9)

Asn Asn Ala Tyr (SEQ ID NO: 10)

Ser Ser Gly Thr Lys Tyr Trp-Val- (SEQ ID NO: 11);

where the bracketed amino acids represent alternatives to the preceding amino acid and a "-" represents an unidentified amino acid;

for use in human or veterinary medicine.

In particular, there is provided the protein for the treatment or prevention of cancer in a human or other mammal.

There is also provided the use of the isolated and purified protein of the first or second aspects of the invention, or fruit bromelain protease in the preparation of an anti-cancer agent.

As a result of this anti-cancer activity, the CCX2 protein or fruit bromelain protease may be used in a method for the treatment of cancer, the method comprising administering to a patient an effective amount of the isolated and purified protein of the first aspect of the invention.

It is known that the bromelain mixture has anti-cancer activity and, as discussed in our earlier application WO-A-9500169, this appears to arise from bromelain's ability to affect intracellular signalling pathways, in particular, pathways which are modulated by MAP kinases. It is therefore possible that this is the mechanism of action of the protein of the present invention. However, the present invention is not dependent upon the correctness or otherwise of this theory.

Ras proteins help relay signals from growth-factor receptors on the surface of cells to transducer molecules to stimulate cell proliferation or differentiation. Oncogenic (or mutant) ras genes produce defective ras proteins that have acquired independence from externally supplied growth factors and, at the same time, may no longer respond to external growth-inhibitory signals. Mutant ras proteins are thus persistently hyperactive and their unbridled catalytic activity has a detrimental effect on the control of cell growth. Oncogenic ras genes therefore promote cancer and tumour formation by disrupting the normal controls on cell proliferation and differentiation. Approximately 30% of human cancers have mutations in a ras gene.

One of the transducer molecules which are activated by ras are the mitogen-activated protein (MAP) kinases (also called extracellular-signal regulated kinases [ERKs]) which transduce growth signals to the nucleus. WO-A-9500169, FIGS. 2 to 6 show that bromelain can prevent activation of the MAP kinases, ERK-1 and ERK-2. Given that signals transmitted by ras can be blocked via MAP kinase, the bromelain mixture would be expected to block cancer and tumour growth and it is possible that the protein of the present invention also works by this mechanism of action.

An alternative explanation is that the protein of the present invention acts by activating the innate immune system. The immune response has two functional divisions: the innate immune system and the adaptive immune system. The innate immune response is mediated by macrophages, natural killer cells and neutrophils. The adaptive immune response is mediated by B and T cells. When a pathogen invades the body, both the adaptive immune response and the innate immune response are activated. Innate immunity provides the first line of defence against infectious agents and most potential pathogens before they establish infection. During this initial phase of innate immunity, the adaptive immune response is developing. If the first defences are breached, the adaptive immune system should be sufficiently developed to produce a specific reaction to the infectious agent, which normally eradicates this agent. The innate immune system is also critically important in killing tumour cells.

The protein of the present invention has been shown to activate macrophages and natural killer cells (NK), critical mediators of the innate immune system important for controlling tumour growth. The protein has also been shown to increase interferon-γ-mediated nitric oxide (NO) production. Various publications have linked NO production to anti-tumour activity. For example, Hibbs (1991, *Res. Immunol.*, 142, 565–569) has shown that when macrophages produce NO, they kill tumour cells in vitro. Thus, increased NO production and activation of innate immunity may be the mechanism by which the protein of the present invention acts against tumours. Again, however, the effectiveness of this protein as an anti-tumour agent is not dependent upon the correctness of this proposition.

The protein of the present invention is useful for treating many different types of cancer including solid cancers such as ovarian, colon, breast or lung cancer and melanoma as well as non-solid tumours and leukaemia.

As mentioned above, CCX2 is able to activate NK cells. NK cells are lymphocytes which can recognise and destroy cells infected with various viral, bacterial or parasitic pathogens. They are also able to kill tumour cells by specifically recognising the expression of virus-induced molecules on tumour cells or other molecules associated with tumours. Therefore, because CCX2 is able to activate NK cells, it will also be of use in the treatment or prevention of virus-induced tumours. Examples of such tumours include hepatocellular carcinoma (which may result from hepatitis B virus); non-Hodgkin's lymphoma, nasopharyngeal carcinoma or Burkitt's lymphoma (resulting from Epstein-Barr virus); Kaposi's sarcoma (resulting from cytomegalovirus in HIV-infected patients); T-cell leukaemia (resulting from human T cell lymphotropic virus); and cervical carcinoma (resulting from human papilloma viruses such as HPV16 and HPV18). Again, because of the high degree of homology, fruit bromelain protease is likely to have the same activity as the CCX2 protein.

In addition to its use as an anti-tumour agent, the ability of the protein of the invention to activate the innate immune response suggests that it or fruit bromelain protease would also be of use in situations where the adaptive immune response, such as B or T cell responses, are not fully functional. This may occur in many secondary immunodeficiencies which may arise because of malnutrition, infection (for example HIV and malaria), tumours (for example lymphoid, myeloma and other), trauma (for example burns, wounds and surgery), medical treatment (for example with drugs such as steriods, cyclosporin and cyclophosphamide), protein loss (such as in diarrhoea and burns), genetic abnormalities (such as those found in combined immunodeficiency patients who lack T and/or B cells), diabetes and old age.

The present inventors have also shown that the protein of the present invention is capable of increasing interferon-γ-mediated NO production. Therefore, CCX2 or fruit bromelain protease may be used to treat diseases or conditions which respond to increased NO production.

NO has a critical role in host defence against infection. NO and its derivatives have potent anti-microbial activity against many pathogens including fungi, bacteria and viruses. Therefore, the protein may be administered to patients receiving chemotherapy to protect against opportunisic infections. It may also be used to treat pathogenic infections including parasites, such as Babesia, Brugia, Cryptosporidium, Encephalitoxoon, Entamoeba, Leishmania, Naegleria, Ochocerca, Opisthorchis, Plasmodium, Schistosoma, Toxoplasma and Trypanosoma. Bacteria affected by NO inlcude Bacillus, Brucella, Burkholderia, Clostridium, Ehrlichia, Francisella, Klebsiella, Legionella, Listeria, Micrococcus, Pseudomonas, Rickettsia, Salmonella, Staphylococcus, Yersinia, Chlamydia especially *C. trachomatis* and mycobacteria such as *M. avium, M. leprae* and *M. tuberculosis*. NO has activity against fungi such as Aspergillus, Candida, Cryptococcus, Histoplasma, Pneumocystis and Saccharomyces and against viruses, for example, Coxsackievirus, Ectomelia virus, Encephalomyocarditis virus, Epstein-Barr virus, Herpes simplex virus, Human immunodeficiency virus type 1, Japanese encephalitis virus, mouse hepatitis virus, parvovirus, poliovirus, rabies virus, simian virus 40, vaccinia virus and vesicular stomatitus virus (Fang, 1997, *ASM News*, 63, 668–673).

The activity of the CCX2 protein in increasing NO production complements its immunostimmulant activity and means that it can be used as an antimicrobial agent against parasites, bacteria, fungi and viruses such as those listed above.

Thus, in further aspects, the invention provides the CCX2 protein or fruit bromelain protease for use as an antimicrobial agent and the use of the CCX2 protein or fruit bromelain protease in the preparation of an antimicrobial agent.

The protein will usually be formulated before administration to patients and so, in a further aspect of the invention there is provided a pharmaceutical or veterinary composition comprising the isolated and purified protein of the first aspect of the invention together with a pharmaceutically or veterinarily acceptable excipient.

The protein may be administered by a variety of routes including enteral, for example oral, nasal, topical, buccal, or anal administration or parenteral administration, for example by the intravenous, subcutaneous, intramuscular or intraperitoneal routes.

In many cases, the oral route may be preferred as this is often the route which patients find most acceptable. The oral route may be particularly useful if many doses of the protein are required as will often be the case in the treatment of cancer.

When oral adminstration is chosen, it may be desirable to formulate the protein in an enteric coated preparation in order to assist its survival through the stomach. Alternatively, another orally administrable dosage form may be used, for example a syrup, elixir or a hard or soft gelatin capsule, either of which may be enteric coated.

However, if it is intended to administer only a single dose of the protein, it may be more convenient to use a parenteral route.

For parenteral adminstration, the protein may be formulated in distilled water or another pharmaceutically acceptable solvent or suspending agent.

A suitable dose of the protein to be administered to a patient may be determined by the clinician. However, as a guide, a suitable dose may be from about 0.5 to 100 mg per kg of body weight. It is expected that in most cases, the dose will be from about 1 to 50 mg per kg of body weight and preferably from 1 to 20 mg per kg of body weight. For a man having a weight of about 70 kg, a typical dose would therefore be from about 70 to 7000 mg.

BRIEF DESCRIPTION OF THE DRAWINGS

The invention will now be further described with reference to the following examples and to the drawings in which.

EXAMPLES

Example 1

Purification of Bromelain Proteins a. Materials

Figure 1:
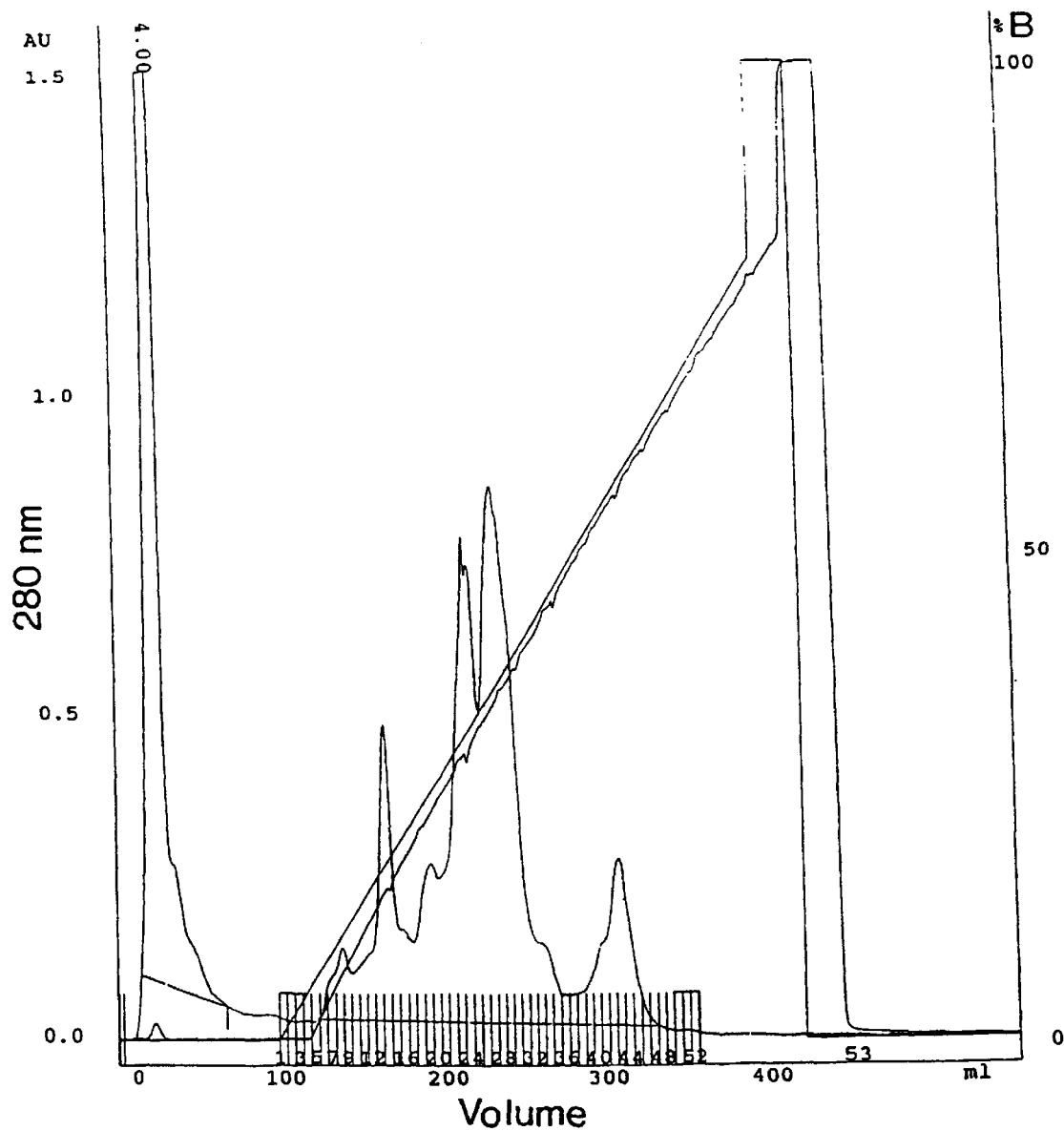
FIG. 1 is an ultra violet elution profile of crude bromelain after cation exchange chromatography on SP Sepharose high performance media.

Bromelain was obtained from Solvay Enzymes Inc. (Germany). Fast Flow S Sepharose, Pharmalyte 3-10, Ampholine 9-11, Ready Mix IEF (acrylamide, bisacrylamide) and IEF markers were obtained from Pharmacia Biotech. Precast 4–20% acrylamide gels and broad range molecular weight markers were obtained from Bio-Rad Laboratories. All other reagents were of analytical grade and obtained from either Sigma Chemical Co. or British Drug House.

b. Proteinase Assay

The proteolytic activity of bromelain was determined by use of an in-house microtitre plate based assay using the synthetic substrate Z-Arg-Arg-pNA. This assay was based on that described by Filippova et al in *Anal. Biochem.*, 143, 293–297 (1984). The substrate was Z-Arg-Arg-pNA as described by Napper et al in *Biochem. J.*, 301, 727–735, (1994).

c. Protein Assay

Protein was measured using a kit supplied by Bio-Rad that is a modified method of Lowry et al (*J. Biol Chem.* (1951) 193, 265–275). Samples were compared to bovine serum albumin standards (0 to 1.5 mg/ml) prepared in either 0.9% saline or 20 mM acetate buffer pH 5.0, as appropriate.

d. Preparation of Bromelain

All the following steps were performed at ambient temperature (20 to 25° C.). A solution of bromelain (30 mg/ml) was prepared by dissolving 450 mg of powder in 15 ml of 20 mM acetate buffer (pH 5.0) containing 0.1 mM EDTA, sodium. The solution was dispensed into 10×1.5 ml microcentrifuge tubes and centrifuged at 13,000×g for 10 minutes to remove insoluble material. The clear supernatants were pooled and used for chromatography.

e. Fast Flow SP-Sepharose High Performance Chromatography

A Fast flow SP-Sepharose column was prepared by packing 25 ml of media into an XK 16/20™ column (Pharmacia Biotech) and equilibrated with 20 mM acetate buffer (pH 5.0) containing 0.1 mM EDTA on an FPLC™ system at 3 ml/min. 5 ml of bromelain solution was injected onto the column. Unbound protein was collected and the column washed with 100 ml of acetate buffer. Protein bound to the column was eluted with a linear gradient of 0 to 0.8 M NaCl in acetate buffer over 300 ml. 5 ml fractions were collected throughout the gradient and FIG. 1 shows a typical U.V. chromatogram of crude bromelain obtained from this procedure.

Figure 2:
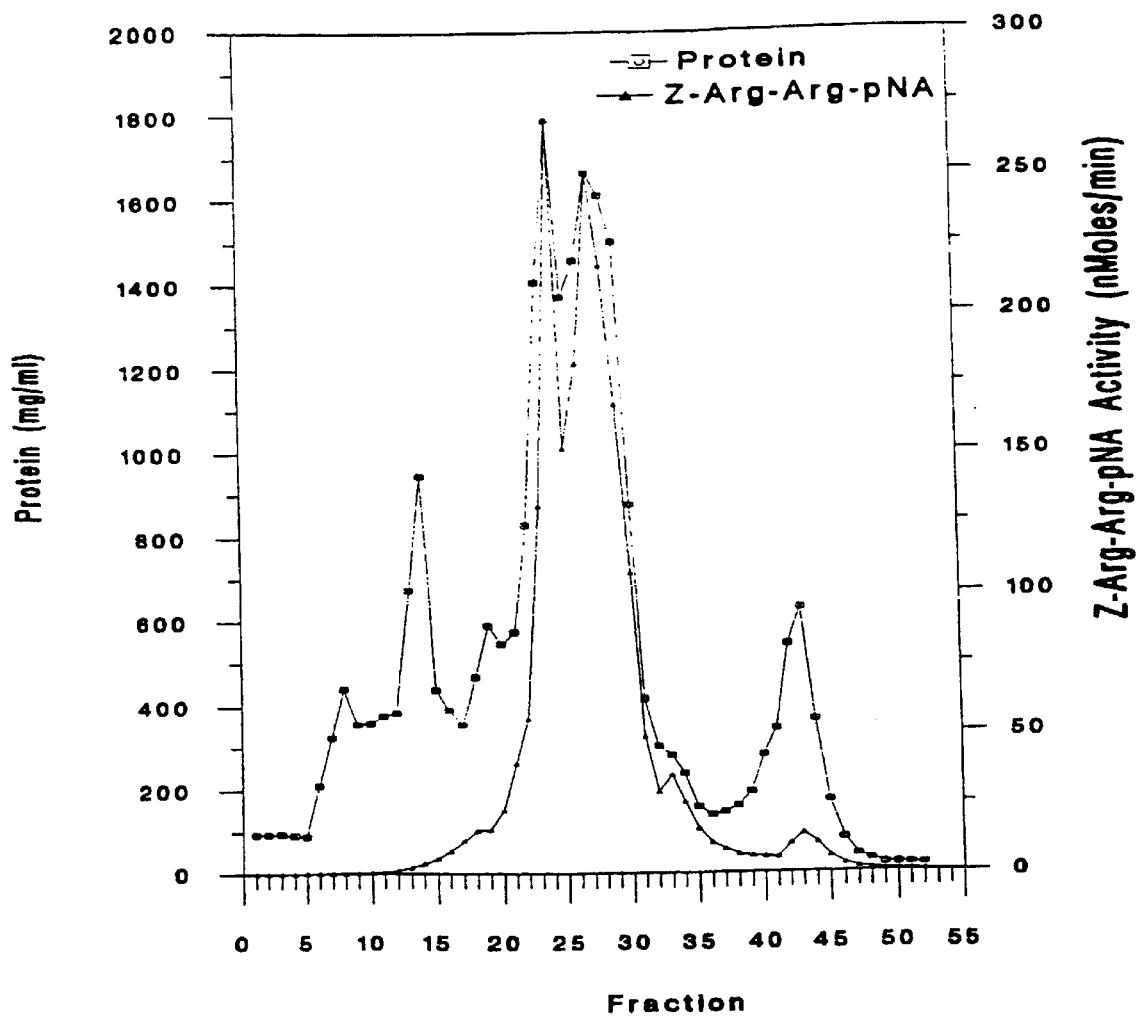
FIG. 2 is a plot showing the proteolytic activity and the protein content of bromelain fractions after cation exchange chromatography on SP Sepharose high performance media.

The fractions were then analysed for protein and proteolytic activity as described above and FIG. 2 shows the proteolytic activity against the synthetic peptide Z-Arg-Arg-pNA and the protein content of the individual fractions. The protein content profile closely mirrors that of the U.V., as expected, but the main proteolytic activity is confined to the two major peaks that correspond to that of stem bromelain proteinase (SBP). Small activities are observed in other areas of the chromatogram that may corresponds to other proteinases distinct from stem bromelain, such as the later eluting Ananain and Comasain (CCS).

The main peaks identified from the U.V. profile were pooled from three successive runs and named as indicated in Table 1. Pooled fractions were used for physico-chemical characterisation. Pooled fractions were concentrated by ultrafiltration and buffer exchanged using PD10 columns into isotonic saline (0.9% w/v NaCl). The protein content and Z-Arg-Arg-pNA activity were calculated prior to biological testing and are shown in Table 2.

TABLE 1

Summary of Pooled Fractions from SP Sepharose HP Fractionated Bromelain (QC2322)

| Component | Description | Fractions Pooled (Inclusive) |
|---|---|---|
| CCT | Flow through (unbound components) | Unbound column flow through |
| CCV | First peak off column | 8–9 |
| CCX | Second sharp peak off column | 13–14 |
| CCZ | Small peak on ascending edge of the third main stem bromelain peak | 19–20 |
| CCY | First main stem bromelain peak | 23–24 |
| CCW | Second main stem bromelain peak | 27–29 |
| CCU | Small peak on descending edge of the second main stem bromelain peak | 33–34 |
| CCS | Last double peak off column | 39–44 |

TABLE 2

Calculated Protein Content and Z-Arg-Arg-pNA Activity of Pooled Fractions used for Testing Biological Activity.

| Pooled Fraction | Z-Arg-Arg-pNA Activity (μMoles/min/ml) | Protein content (mg/ml) |
|---|---|---|
| CCT | 11.30 | 1.00 |
| CCV | 9.78 | 1.00 |
| CCX | 71.71 | 1.00 |
| CCZ | 688.81 | 1.00 |
| CCY | 1500.0 | 0.574 |
| CCW | 1500.0 | 0.543 |
| CCU | 1500.0 | 0.421 |
| CCS | 379.76 | 1.00 |

The pooled fractions were processed for analysis as described below.

f. Processing of Pooled Fractions

The proteolytic activity and protein content of pooled fractions were determined and the concentrations adjusted to approximately either 1.4 mg/ml of protein or 105 nmoles/min/ml of proteinase activity using a Filtron™ stirred cell containing an ultrafiltration membrane of nominal molecular weight cut-off of 10 kDa. The fractions were then buffer exchanged using PD10™ columns (Pharmacia Biotech) into isotonic saline (0.9% w/v NaCl), sterile filtered (0.2 μm) and adjusted for protein content or proteolytic activity.

g. Sodium Dodecyl Sulphate Polyacrylamide Gel Electrophoresis (SDS-PAGE)

Pooled FPLC™ samples were analysed by sodium dodecyl sulphate polyacrylamide gel electrophoresis (SDS-PAGE) on precast 4 to 20% T gradient gels. Samples were prepared for electrophoresis by acid precipitation in which 100 μl was mixed with an equal volume of 20% w/v trichloroacetic acid (TCA). Precipitated protein was collected by centrifugation at 13,000×g for 10 minutes and the supernatant discarded. The pellet was washed twice with 0.5 ml of diethyl ether and left to dry in air at ambient temperature. The pellets were then dissolved in 300 μl of SDS-PAGE sample buffer (62.5 mM Tris-HCl pH 6.8 containing 10% v/v glycerol, 2% w/v sodium dodecyl sulphate and 40 mM dithiothreitol) and heated at 95° C. in a water bath.

SDS-PAGE broad range molecular weight standards diluted 1:20 in SDS-PAGE sample buffer were treated similarly and run with the samples. Gels were run on a mini Protean II™ electrophoresis system as previously described by the manufacturer (Bio-Rad) at 240 V and until the dye front reached the end of the gel (30 to 45 min).

After electrophoresis, separated proteins were stained overnight with orbital mixing in a solution of 0.075% w/v colloidal brilliant blue G-250 containing 1.5% v/v phosphoric acid, 11.25% w/v ammonium sulphate and 25% v/v methanol. Gels were destained, to obtain a clear background, in a solution of 25% v/v methanol and 10% v/v acetic acid.

Results

Figure 3:
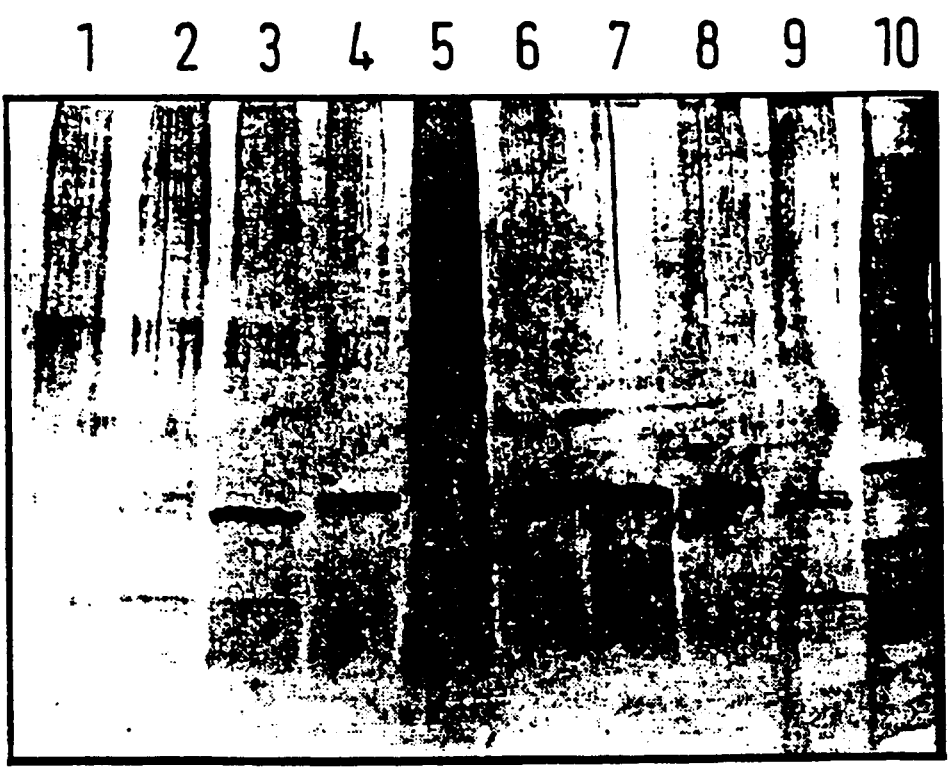
FIG. 3 is an SDS-PAGE of SP Sepharose high performance chromatography pooled fractions run on 4–20% T gradient gels with lanes 1 to 4 and 6 to 9 containing fractions CCT, CCV, CCX and CCZ and CCY, CCW, CCU and CCS respectively and lanes 5 and 10 containing molecular weight markers.

The purity of fractions is shown by SDS-PAGE in FIG. 3. All of the pooled fractions except the column flow through (CCT) showed that the major protein present was of molecular weight between approximately 25–28 kDa. This corresponds to the molecular weight of cysteine proteinases isolated from bromelain by other authors (Rowan et al, *Methods in Enzymology*, (1994), 244, 555–568). The purity of fractions CCX, CCZ, CCY and CCW appears to be high. Minor components of lower molecular weight can be observed in some fractions, particularly CCT, CCV, CCX and CCS. Pooled fractions CCU and CCS contain a doublet between 25–28 kDa; the higher gel loadings of fractions CCX, CCZ, CCY, and CCW means that doublet bands may also be present in these fractions. A summary of the components and their calculated molecular weights in pooled fractions, as determined by SDS-PAGE, is shown in Table 3.

Proteins in pooled fractions CCX, CCZ, CCY+CCW and CCU were transferred onto nitro-cellulose after SDS-PAGE by Western blotting and probed with rabbit antisera raised against purified bromelain (results not shown). All protein bands in these pooled fractions were recognised by antibodies in the sera, indicating immunologically similar proteins, probably belonging to the cysteine proteinase family of enzymes.

h. Isoelectric Focusing

Pooled fractions (0.5 to 1.0 mg/ml) were diluted 1:3 with deionised water and run on gradient gels of pH 3 to 11. Gels were cast using Ready Mix IEF™ to produce a 5.5% T, 3% C polyacrylamide gel containing 10% v/v glycerol, 5.0% Pharmalyte 3-10™ and 2.5% Ampholine 9-11™. Briefly, 10 μl of sample and high pI markers were loaded onto the gel after prefocusing at 700 V. Sample entry was at 500 V for 10 min, focusing was at 2500 V for 1.5 hour and band sharpening at 3000V for 10 min. After electrophoresis the proteins were fixed with a solution of 20% w/v TCA for 30 min, washed in destain for 30 min to remove TCA and stained with brilliant blue G-250 as described for SDS-PAGE (see above).

TABLE 3

Summary of the Molecular Weights of Proteins found in SP Sepharose HP Pooled Fractions as Determined by SDS-PAGE.

| Pooled Fraction | Molecular Weight (kDa) of Major Protein Band(s) | Molecular Weight (kDa) of Minor Protein Bands(s) |
| --- | --- | --- |
| CCT | 76.03 | 15.07 |
| CCV | 15.07, 25.85, 28.28, 76.03 | |
| CCX | 25.08 | 15.07, 76.03 |
| CCZ | 27.45 | 13.37, 16.49, 76.03 |
| CCY | 27.45 | 6.5 |
| CCW | 27.45 | |
| CCU | 27.45, 28.28 | |
| CCS | 15.07, 25.85, 27.45 | |

Results

Figure 4:
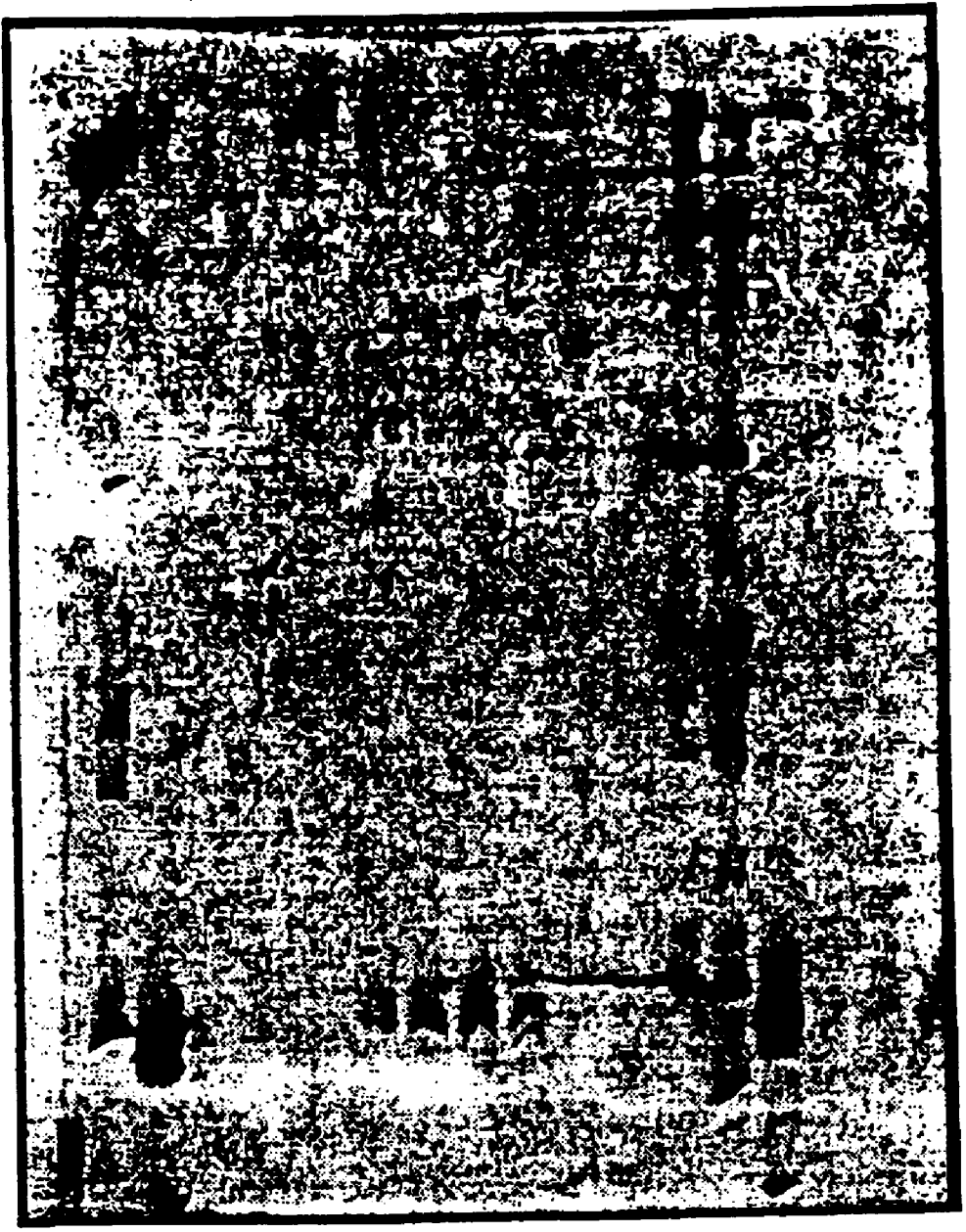
FIG. 4 shows isoelectric focussing of pooled fractions run on pH 3–11 gradient gels with Lanes 1, 11 and 12 showing high IEF markers, Lanes 2 and 13 showing crude bromelain and Lanes 3 to 10 showing fractions CCT, CCV, CCX, CCZ, CCY, CCW, CCU and CCS respectively.

FIG. 4 shows that all fractions except CCX contained basic proteins focusing beyond the 9.3 pI marker. Localised charge interactions with the chromatographic media functional groups may explain why proteins of pI 3.8 and 3.85 in CCX, adsorbed onto a cation exchange resin at pH 5.0. CCZ was present as a single band of pI 9.7, whilst pooled fractions CCY, CCW, and CCU contained multiple bands of isoelectric points in the range pH 9.5–9.8. At least part of this heterogeneity can be explained by variation in the carbohydrate moiety of a common bromelain protein backbone. The values are in agreement with those reported in the literature of pI 9.45–9.55 for stem bromelain (Rowan et al, *Methods in Enzymology,* (1994), 244, 555–568). Pooled fractions CCS contains two basic protein of pI greater than 10.25. Estimates by extrapolation give pIs of 10.4 and 10.45. These correspond to ananain and comasain, and are in agreement with other estimates (Rowan et al, as above) of pIs greater than 10. The pIs of proteins in each of the pooled fractions are summarised in Table 4.

TABLE 4

Summary of the estimated Isoelectric points of Proteins found in SP Sepharose HP Pooled Fractions.

| Pooled Fractions | Isoelectric Points of Proteins |
| --- | --- |
| CCT | Not detected |
| CCV | Not Detected |
| CCX | 3.8, 3.85 |
| CCZ | 9.7 |
| CCY | 9.6, 9.7 |
| CCW | 9.57, 9.6, 9.7 |
| CCU | 9.57, 9.6, 9.75 |
| CCS | 10.4, 10.45 | i. Western Blotting

Samples run by SDS-PAGE as described above were transferred onto a nitro-cellulose membrane (0.45 μm pore size) using a Transblot™ apparatus (Bio-Rad) at 100 V for 1 hour in Towbin buffer as described by the manufacturer. After transfer of protein, the membrane was rinsed in distilled water and then dried in an incubator at 60° C. overnight. After drying, the membrane was blocked for 30 min in a 1% solution of BSA in 20 mM Tris-HCl (pH 7.5) containing 500 mM NaCl (Tris buffer), followed by two 10 min washes in Tris buffer. The membrane was then probed with a 1:50 dilution of anti-bromelain antiserum (rabbit) in Tris buffer, containing 0.05% v/v Tween 20™, for 2 h. The blot was developed after washing three times in Tris buffer containing Tween 20™ and incubating with anti-rabbit horse radish peroxidase for two hours. Immuno-reactive bands were visualised by incubation with 4-chloronapthol substrate.

Example 2

In vitro Growth Inhibition of Bromelain Fractions Against a Panel of Human Tumour Cell Lines The aim of the study was to determine the comparative growth inhibitory properties of fraction CCX, stem bromelain protease (SBP) and crude bromelain against a panel of fifteen human tumour cell lines representative of five of the most common solid cancers in humans: ovarian, colon, breast, lung and melanoma.

Cell lines were trypsinised and single viable cells were seeded into 96-well microtitre plates at a density of $4 \times 10^3$ per well in 160 μl growth medium. After allowing for attachment overnight, samples were then added to quadruplicate wells in 40μl growth medium to give a range of final concentrations in wells of 50, 10, 2.5, 1 and 0.25 μg/ml. Eight wells were allocated as control untreated cells. Extracts were diluted immediately prior to addition to cells in sterile water. Extract exposure was for 96 hours whereupon cell number in each well was determined using staining with 0.4% sulforhodamine B in 1% acetic acid as described previously (Kelland et al, *Cancer Res.,* 53, 2581–2586 (1993)). 50% inhibitory concentrations ($IC_{50}$ in μg/ml) were then calculated from plots of concentration versus % control absorbance (read at 540 nm).

Results

Figure 5:
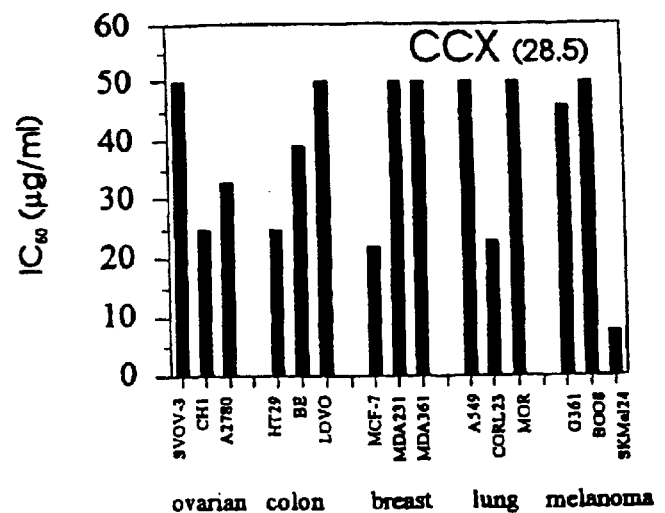
FIG. 5 is a series of plots showing the effect of fraction CCX, stem bromelain protease (SBP) and crude bromelain on the growth inhibition of tumour cells in vitro. Results are presented by equivalent protein fraction. Values in parenthesis represent the proteolytic activity (Z-Arg-Arg-pNA) of each sample.
Figure 5:
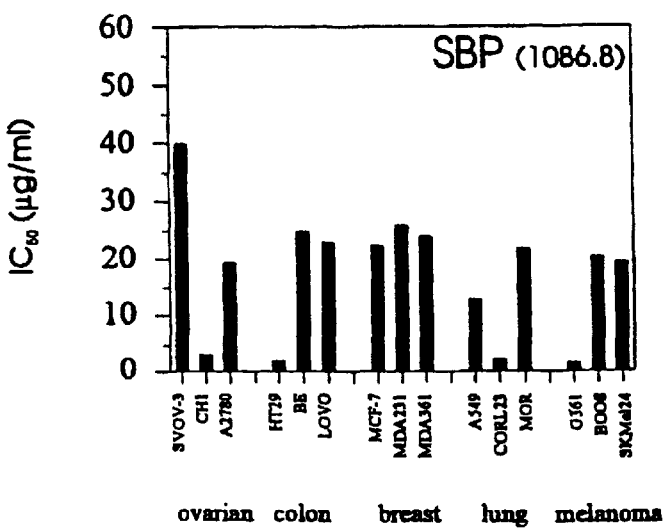
Figure 5:
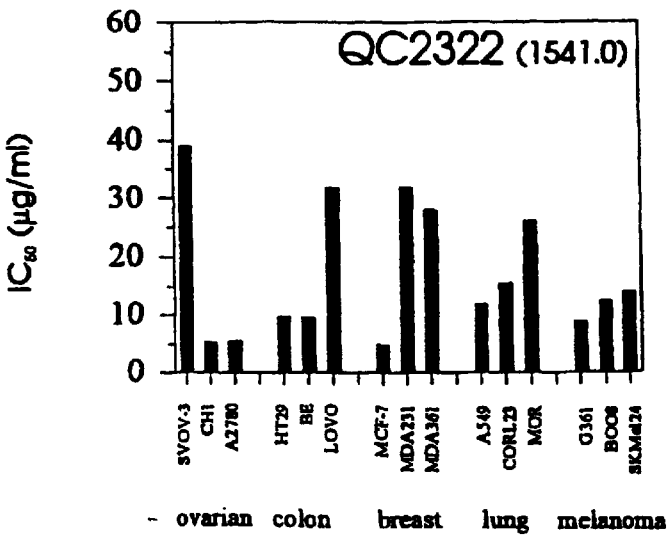

All extracts were successfully dissolved and $IC_{50}$ values are shown in FIG. 5. As can be seen from FIG. 5, fraction CCX showed in vitro potency against many of the tumour cell lines. It showed differential activity against most cell lines, being the most potent against SKMel24 (melanoma) and displaying intermediate activity against A2780 and CH1 (ovarian) HT29 (colon), MCF-7 (breast) and CORL23 (lung). CCX had negligible activity against other cell lines including SKOV-3 (ovarian), LOVO (colon), MDA231, MDA361 (breast) A549, MOR (lung), G361 and BOO8 (melanoma).

The selectivity of the effect of CCX against some tumour cell lines, but not others, suggests that CCX has a specific mode of action and does not act as a non-specific cytotoxic agent.

From FIG. 5, SBP and crude bromelain appear to have an equal or greater effect on the tumours than the CCX fraction. The method used in this example relies on the detection of cells immobilised to wells of a microtitre tray. Growth inhibitory activity is determined by staining of cells following treatment with bromelain fractions. Dead or dying cells become detached from the wells and therefore do not stain. Cells may also be removed from wells by treating with high concentrations of enzymes such as trypsin; a process referred to as "trypsinisation". It is therefore possible that growth inibitory activity of the CCX fraction is caused by a non-specific removal of cells from wells arising from proteolytic activity rather than a specific "anti-cancer" effect.

In view of this, the results given in FIG. 5 were adjusted for the proteolytic activity of each of the fractions. The adjusted results are given in FIG. 6.

Figure 6:
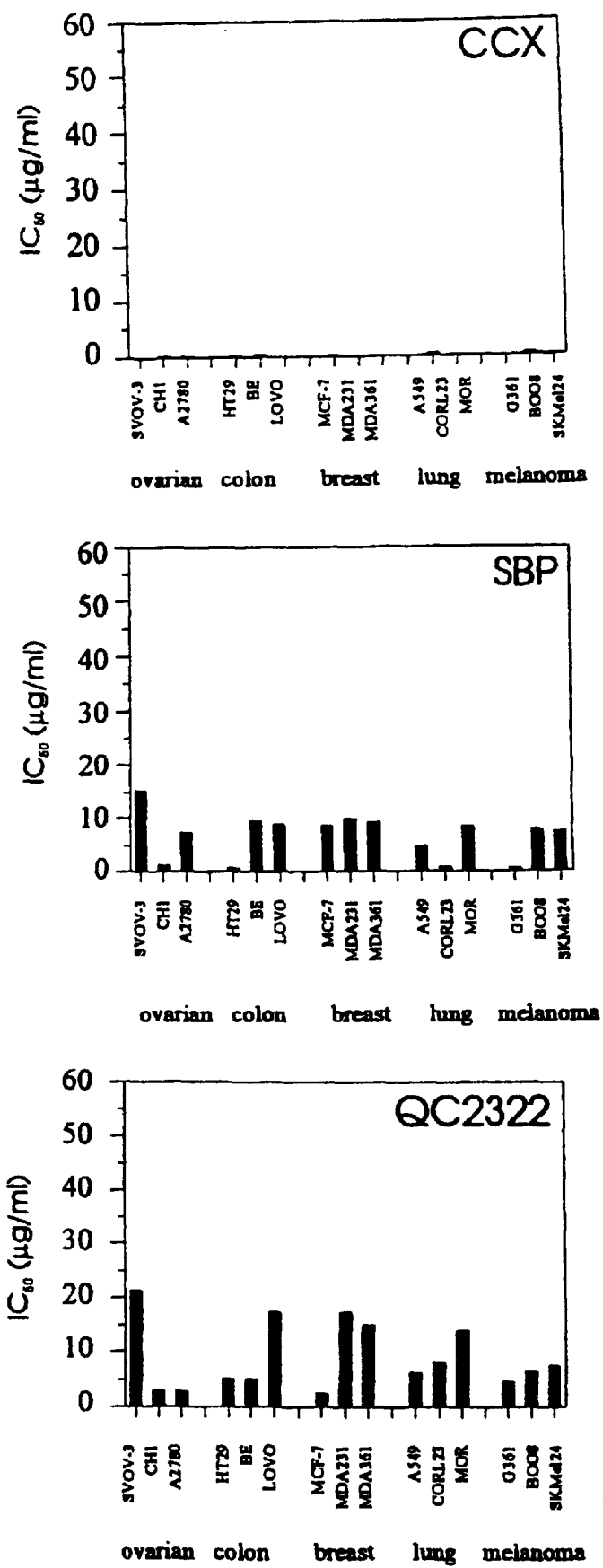
FIG. 6 is a series of plots similar to those in FIG. 5 but in which the data has been transformed to represent equivalent proteolytic activity of the CCX fraction and stem bromelain protease.

Using this interpretation, it can be seen from FIG. 6 that a somewhat different analysis of the results is obtained. Once the proteolytic activity of each of the fractions has been taken into account, the fraction which seems to have the most significant anti-cancer activity is fraction CCX.

Figure 7:
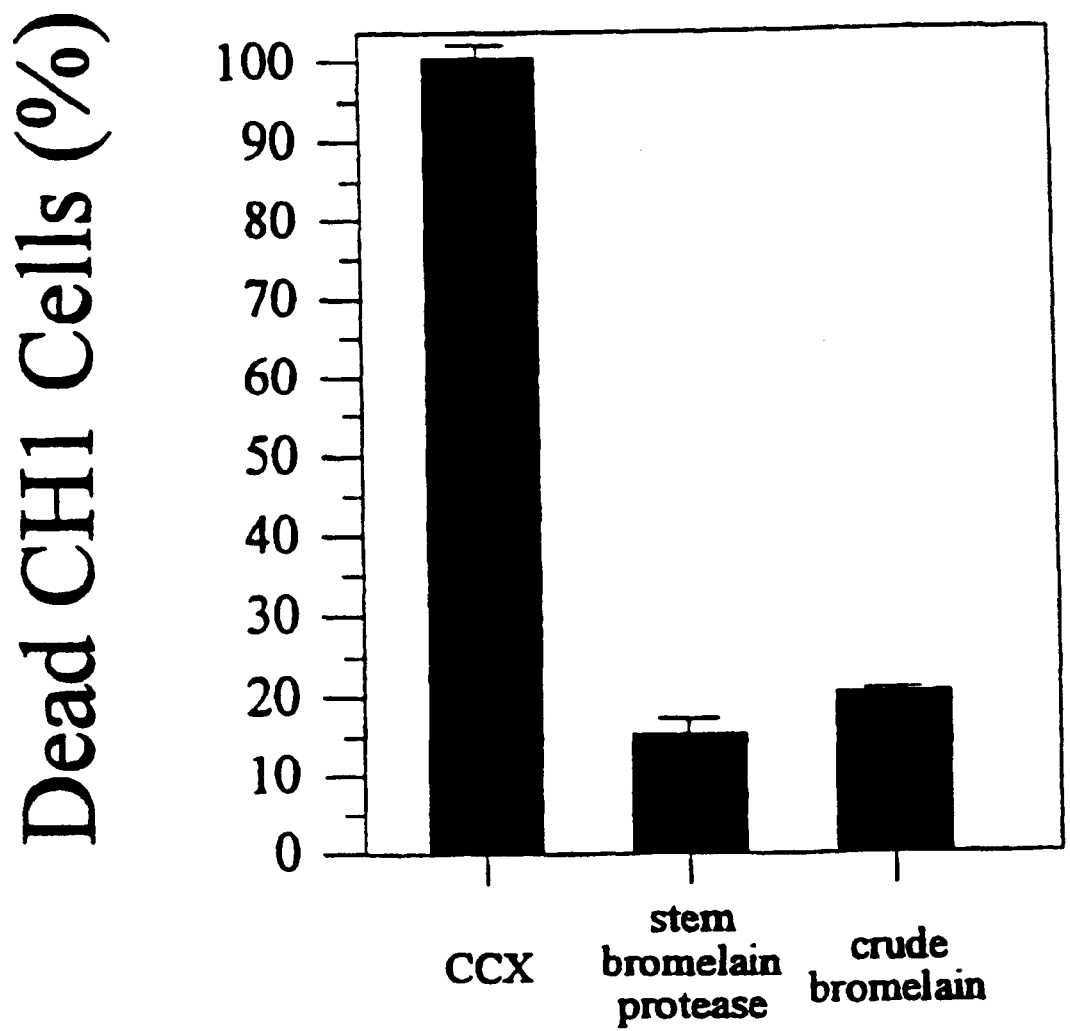
FIG. 7 is a comparison of growth inhibitory activity of stem bromelain protease and fraction CCX against CH1 ovarian tumour growth in vitro.

The ability of CCX, which has negligible Z-Arg-Arg-pNA (protease) activity, to inhibit growth of the cancer cells would suggest a specific anti-cancer activity rather than non-specific removal of cells from wells. To confirm that CCX does indeed have the most potent growth inhibitory activity, stem bromelain protease and crude bromelain were diluted to contain equivalent proteolytic activity to CCX and tested for their ability to inhibit CH1 ovarian tumour growth. FIG. 7 confirms that CCX has the most potent growth inhibitory activity.

Example 3

Anti-tumour Efficacy of CCX Extract Against the CH1 Human Ovarian Carcinoma Xenograft in vivo Since fraction CCX displayed anti-tumour activity in vitro, we next wished to investigate whether fraction CCX would display anti-tumour activity in animal models in vivo. Studies were conducted by Dr Lloyd Kelland, CRC Centre for Cancer Therapeutics at The Institute of Cancer Research.

Methods a. CCX

Fraction CCX, corresponding to the second sharp peak off the chromatography column, was prepared as described in Example 1. Fraction CCX was supplied at a concentration of 5 mg/ml in 0.9% saline and stored at −20° C. until required.

b. CH1 Human Ovarian Carcinoma Xenograft

Female nude (nu/nu) mice aged 6 to 8 weeks were implanted subcutaneously on their flank with 2 mm$^3$ fragments of the CH1 xenograft tumour originally derived from inoculating mice with the CH1 human ovarian carcinoma cell line. Implantation of tumours was under anaesthesia using halothane. The human CH1 ovarian cell line was chosen because studies conducted in Example 2 showed that this cell line was sensitive to fraction CCX treatment in vitro.

Animals were housed in negative pressure flexible film isolators and maintained on Labsure™ 21% protein diet with access to sterile tap water ad libitum. When tumours had reached an average maximum diameter of 6 to 8 mm, mice were randomised to receive fraction CCX administered intravenously into the tail vein at doses of 12.5, 25 or 50 mg/kg (n=6 animals per dose level). Ten animals were randomised to receive saline alone (controls). Fraction CCX was administered on days 0, 4 and 8 following randomisation of animals and approximately 6 weeks after tumours were implanted.

c. Evaluation of Efficacy of CCX

Mice were monitored daily for signs of drug or tumour-induced stress/toxicity. Under the guidelines for animal experimentation adopted by the CRC Centre for Cancer Therapeutics, no animal is allowed to die from tumour or drug-induced effects; animals are killed painlessly at the onset of moribundity. Tumour diameters (a) and (b) are measured twice weekly using a slide calliper where (a) represents the longest diameter and (b) the longest diameter at right angles to (a).

Tumour volumes (V) were then calculated according to the equation V=a×b2×pi/6 and normalised to the volume at the start of treatment (day 0). Data are presented as Relative Tumour Volumes (RTV) (mean "SEM of all surviving animals at that time point) versus time in days from the start of treatment.

Antitumour effects were assessed in terms of the ratio of mean tumour volume of treated versus control groups (T/C) (on day 11, the time at which control tumours had grown to maximum ethical limits). In addition, growth delays (the difference in days for treated versus control tumours to double in volume) were calculated.

To assess drug-induced toxicity, mice body weights were recorded twice weekly and, at the termination of the experiment, major organ histology was conducted.

d. Statistics

The significance of differences between each treated and control group was assessed using a Student's t-test (independent, two tailed) or by ANOVA (one-way for treatment effect for all groups combined). $P<0.05$ was regarded as significant.

Results

Figure 8:
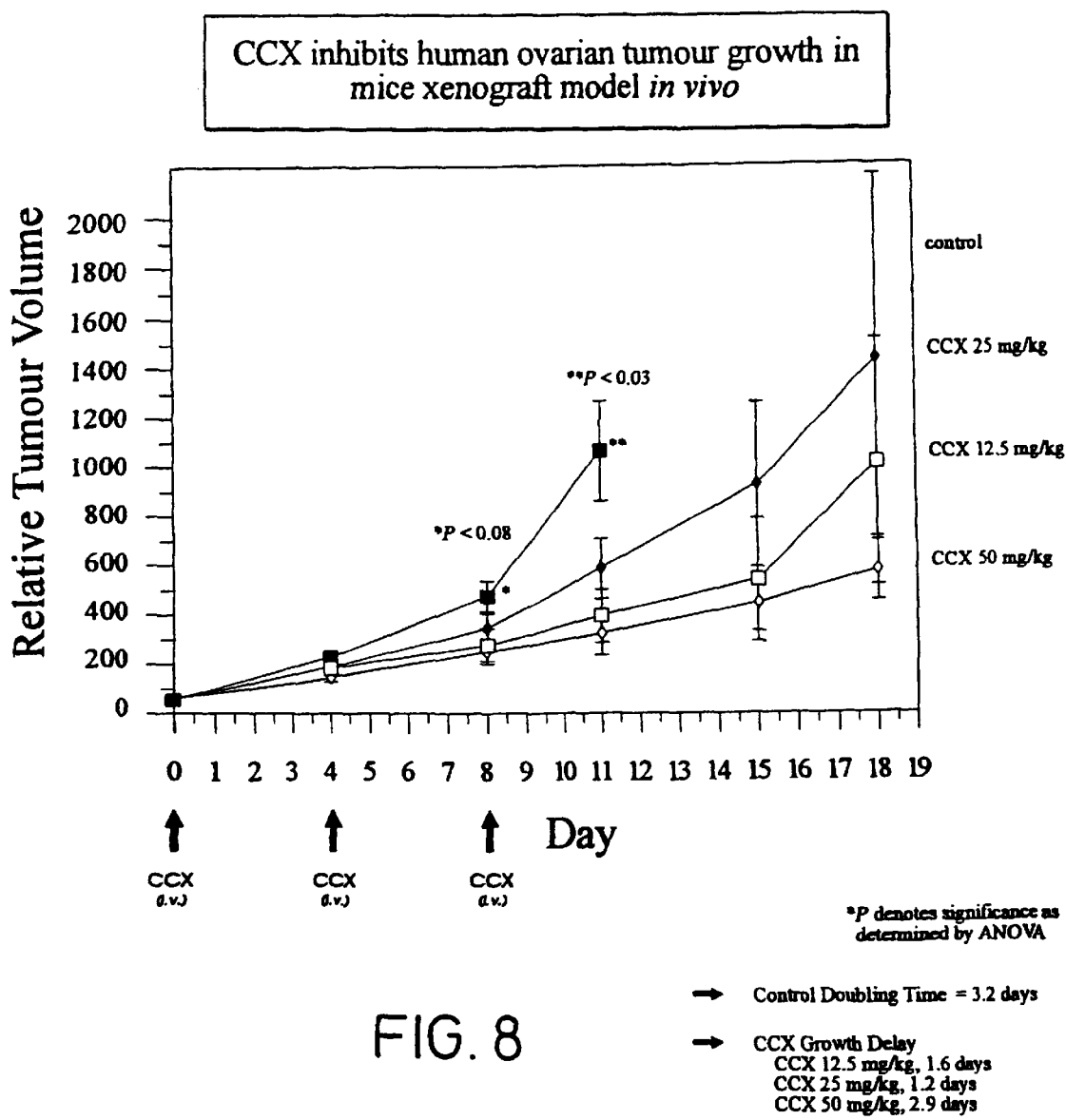
FIG. 8 shows the growth inhibitory activity of various doses of fraction CCX against human ovarian tumours implanted in nude mice. Arrows indicate the day CCX was administered. Day 0 is approximately 4 weeks after tumours were implanted.

FIG. 8 shows that fraction CCX exhibits clear evidence of in vivo anti-tumour activity against the CH1 human ovarian carcinoma at all three doses tested. At day 8, a tumour reduction of 63% was observed in the highest treatment group (50 mg/kg days 0, 4, 8) compared to untreated controls. Since 2 control animals had been removed from the analysis by day 11 due to unacceptably large tumours, the actual maximum reduction in tumour size in the 50 mg/kg group at day 11 may be determined as 70% (assuming RTV values of 1800, the highest RTV value obtained in control animals, to substitute for the removed 2 control animals; p=0.023, t-test; p<0.05 ANOVA).

By day 15, all control animals had been removed from the study, because of large tumours. In contrast, only one animal from each of the CCX treatment groups had been removed. This data indicate that not only does CCX significantly prevent tumour growth, but also substantially increases the life span of animals.

Figure 9:
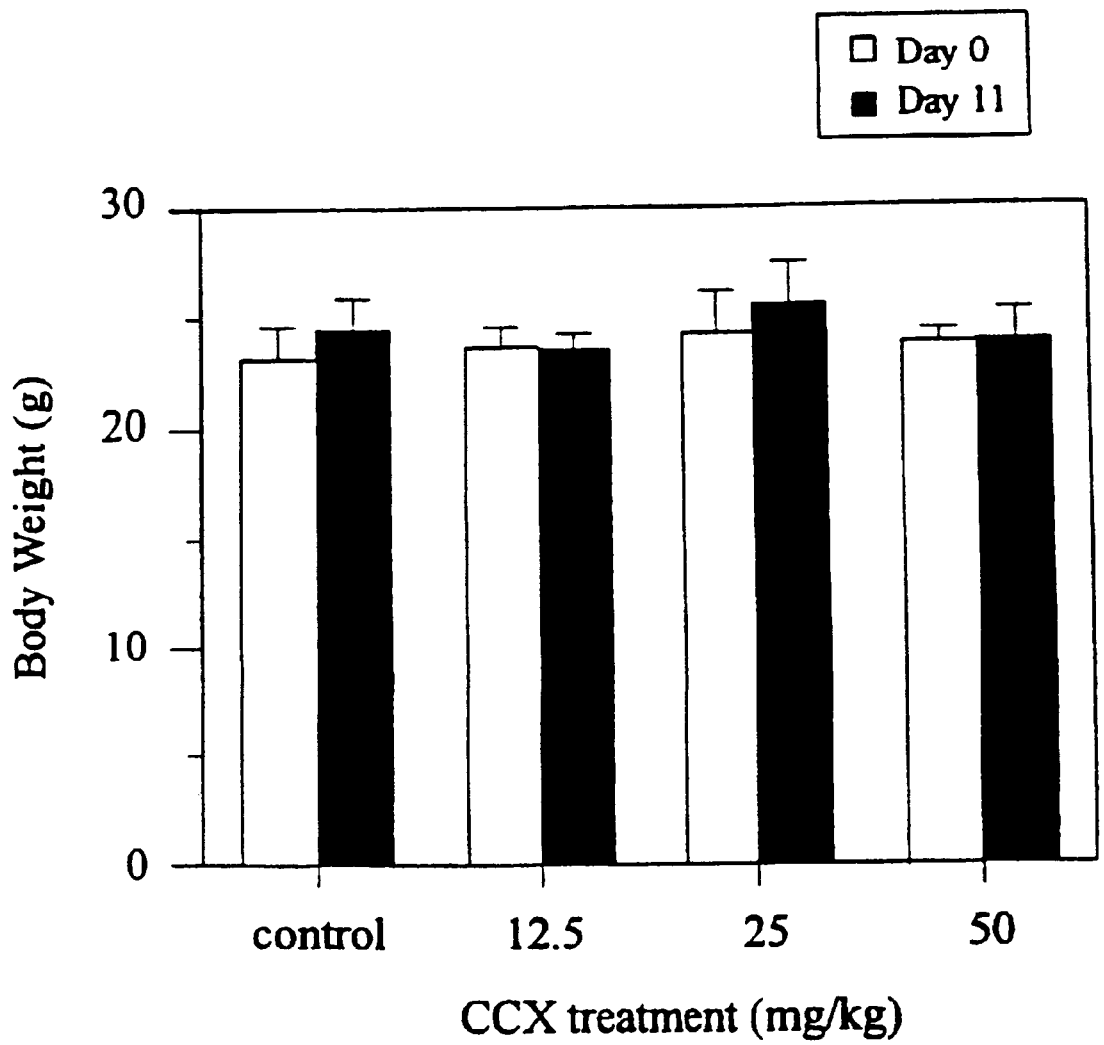
FIG. 9 is a plot which shows that various doses of fraction CCX did not affect the body weight of mice implanted with tumours.

The statistically significant reduction in tumour growth was observed in the absence of any CCX-induced toxicity. There was no significant reduction in animal body weight (FIG. 9). Also, at post mortem, no major organ toxicity was noted. Although, in CCX-treated animals, a slight pink tinge to the whole intestine was noted in all mice except two receiving the lowest (12.5 mg/kg) dose.

Example 4

CCX Increases Nitrate Production by Macrophages and Therefore Can Stimulate Innate Immune Responses In a copending application, we have mentioned that one of the components of bromelain, called CCZ, enhances nitric oxide (NO) production by macrophages. NO is known to be a potent killer of tumour cells and may therefore be of use in cancer therapy.

NO is also a critical mediator of host immune responses. NO related anti-microbial activity has also been shown to be clinically important in humans with intracellular pathogen infections such as mycobacteria, Plasmodium, and Leishmania. In patients with active tuberculosis or malaria, higher levels of NO production correlate with better clinical outcome, consistent with a beneficial role of NO in host defense. NO related biological activities are also readily detectable in macrophages obtained from individuals with a variety of conditions that cause inflammation, including tuberculosis, malaria, AIDS, and rheumatoid arthritis. CCX may therefore stimulate innate immunity by inducing production of the NO metabolite by macrophages to control various intracellular infections.

The nude mice used in the tumour study described in Example 3 do not possess T cells, but do possess macrophages. Therefore it is possible that the anti-tumour effects of CCX observed in Example 3 could be mediated via effects on the innate immune system. We therefore investigated whether CCX could increase NO production by macrophages.

Methods a. Materials

The murine macrophage cell line RAW 264 was stimulated in culture with recombinant IFN-γ (100 U/ml). Nitrite levels in culture supernatants were measured using the Greiss assay (Roach, et al., 1991. *Infection and Immunity* 59: 3935–3944.). NO is an unstable gas which is difficult to measure. Nitrite, however, is a stable end product of NO production which can be easily measured.

b. Treatment of Macrophages

RAW264 macrophages were treated with either CCX (50 μg/ml), crude bromelain (50 μg/ml), stem bromelain protease (50 μg/ml) or mock-treated with saline. Cells were then washed three times to remove the treatment, and then stimulated with IFN-γ.

Results

Figure 10:
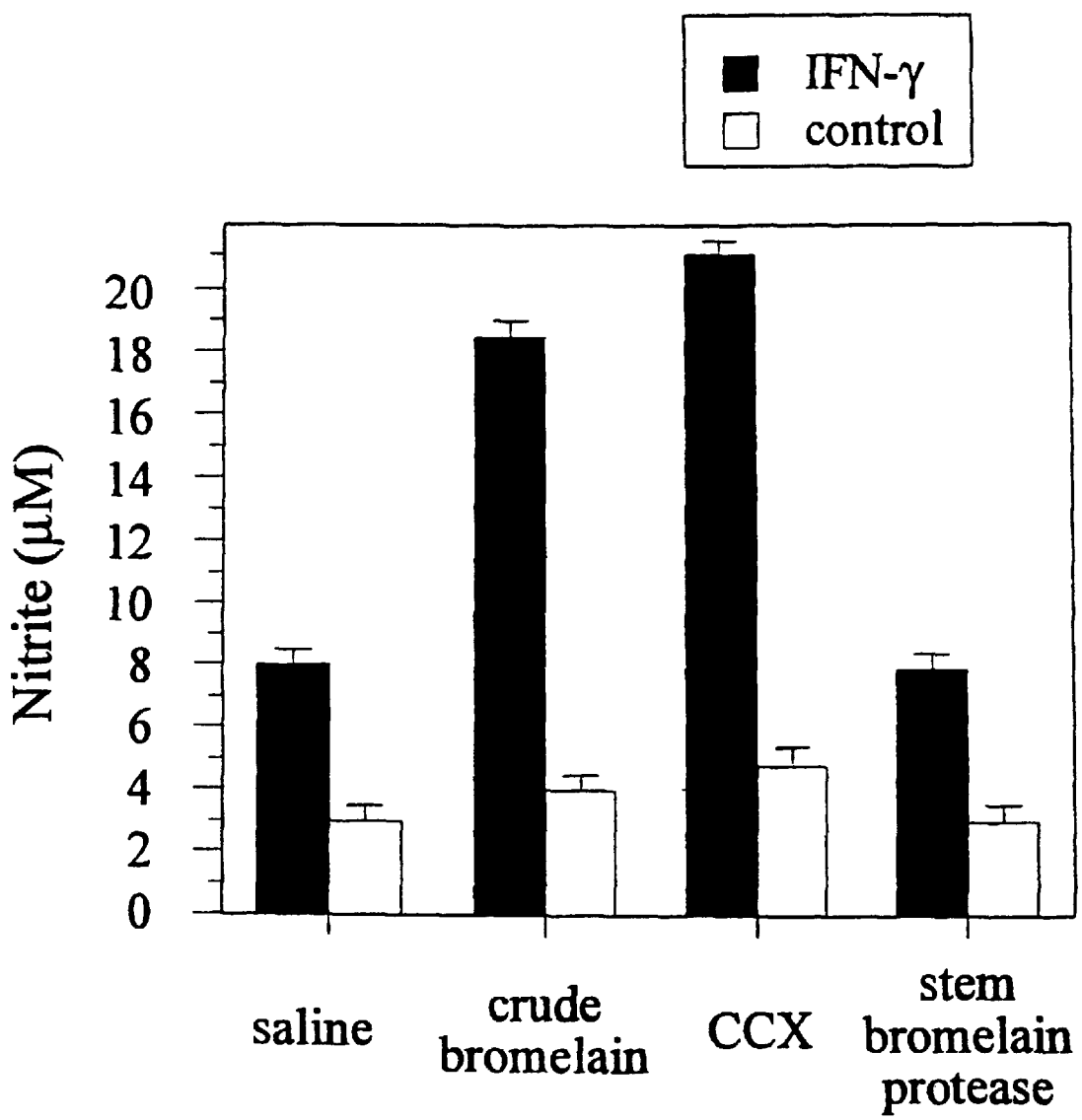
FIG. 10 shows the ability of fraction CCX to increase IFN-γ-mediated nitrite production by macrophages and thus stimulate innate immunity.

Crude bromelain and CCX, but not stem bromelain protease, were found to significantly increase IFN-γ-mediated nitrite production (FIG. 10). In CCX treated cells, the increase in IFN-γ-mediated nitrite production was significantly greater than saline-treated cells suggesting that CCX synergises with IFN-γ to increase NO production. Negligible nitrite was produced when macrophages were stimulated with CCX or bromelain alone, indicating that CCX or bromelain do not activate nitrite production directly. To ensure that potential contaminating endotoxin which may have been present in the CCX mixture was not responsible for the increase in NO, polymyxin B (a potent inhibitor of endotoxin) was included in experiments. The inclusion of polymyxin B did not affect the IFN-γ-induced increase in NO production by CCX-treated cells, indicating that potential contaminating endotoxin was not responsible for the observed effect (data not shown). The ability of CCX to increase NO production provides a possible explanation for the anti-tumour activity of CCX in vivo.

Example 5

CCX Activates NK Cells

In Example 4, we showed that CCX could synergise with IFN-γ to increase NO production by macrophages. CCX may therefore activate the innate immune system and be of use to combat infection, or act as an anti-tumour agent. In this current Example we extend these findings by demonstrating that CCX also activates natural killer (NK) cells, another important component of the innate immune system.

NK cells are lymphocytes which can recognise and destroy cells infected with various viral, bacterial or parasitic pathogens. In addition, NK cells also kill tumour cells by specifically recognising the expression of virus-induced molecules on tumour cells or other molecules associated with tumours. Approximately 20% of tumours in females and 8% in males result from viral infection.

Method

IFN-γ is an important immunological mediator produced by NK cells. It is a potent pro-inflammatory cytokine which activates macrophages by increasing expression of MHC class II molecules. IFN-γ also stimulates the production of other inflammatory mediators, including NO. The activation of macrophages can play a critical role in combating tumour growth and fighting infection by various pathogens.

The effect of CCX on IFN-γ production was investigated in splenocytes obtained from severe-combined immunodeficient (SCID) mice. SCID mice do not possess B or T cells, therefore any IFN-γ produced by SCID splenocytes would originate from NK cells.

Splenocytes were isolated from SCID mice as previously described (Kaye and Bancroft, 1992. *Infection and Immunity* 60:4335–4342). Splenocytes were then treated with CCX (50 μg/ml) or saline, washed and then cultured in either media alone, or in the presence of recombinant IL-12 (100 U/ml) and IL-2 (50 U/ml). IL-12 and IL-2 are potent activators of NK cells.

Culture supernatants were harvested after 24 hours and IFN-γ levels were measured by ELISA (Kaye and Bancroft, 1992. *Infection and Immunity* 60:4335–4342).

Results

Figure 11:
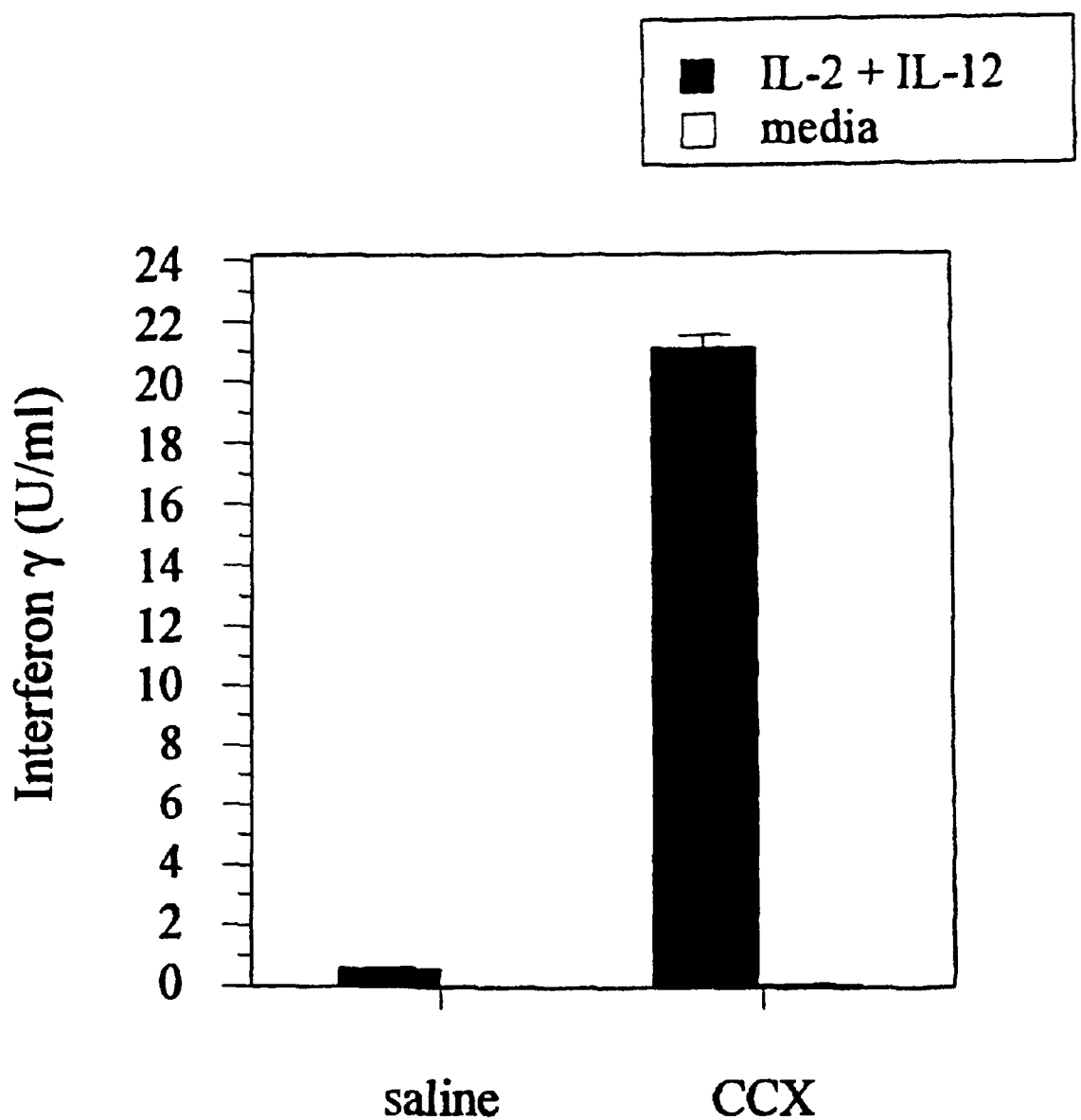
FIG. 11 shows the ability of fraction CCX to increase IFN-γ production in spenocytes obtained from severe-combined immunodeficient (SCID) mice and thus stimulate innate immunity.

CCX significantly increased IL-2 and IL-12-mediated IFN-γ production by SCID splenocytes (FIG. 11). In saline-treated controls, only a small increase in IL-12 and IL-2-mediated IFN-γ production was observed. Negligible IFN-γ was produced when splenocytes were treated with CCX and cultured in the absence of IL-2 and IL-12. This data suggests that CCX does not activate NK cells directly, but synergises with IL-2 and IL-12 to increase IFN-γ production.

To ensure that potential contaminating endotoxin which may have been present in the CCX mixture was not responsible for the increase in IFN-γ, polymyxin B (a potent inhibitor of endotoxin) was included in experiments. The inclusion of polymyxin B did not affect IFN-γ production by CCX-treated cells, indicating that potential contaminating endotoxin was not responsible for the observed effect (data not shown).

The ability of CCX to increase IFN-γ production in splenocytes obtained from SCID mice suggests that CCX activates NK cells and further supports the anti-tumour activity of CCX in vivo.

Example 6

Purification of CCX Proteins

In Examples 1 to 5 above, fraction CCX protein was used in in vitro and in vivo studies. Therefore to confirm that the anti-tumour activity is indeed due to the CCX protein and not due to a minor contaminant in the fraction CCX mixture, we separated out the CCX fraction into its constituent components.

Methods a. Materials

Stem bromelain (3027 GDU/g) was obtained from Polyamine Corporation of Taiwan. SP Sepharose HP, Q Sepharose FF, Phenyl Sepharose HP, Hitrap desalting column, Ampholine PAGplate (pH 3.5–9.0) and broad range IEF markers were purchased from Pharmacia Precast 4–12% acrylamide gels were obtained from Novex and broad range molecular weight markers from Biorad. A DC protein assay kit was obtained from Biorad. Z-Arg-Arg-pNA, Z-Phe-Val-Arg-pNA and Bz-Phe-Val-Arg-pNA synthetic substrates were purchased from Bachem (U.K.) Ltd. All other reagents were of analytical grade and obtained from either Sigma Chemical Co. or British Drug House.

b. Proteinase Assay

The proteolytic activity of crude bromelain, stem bromelain protease, CCX and chromatographic fractions were determined by use of a microtitre plate based assay using the synthetic substrates Z-Arg-Arg-pNA, Z-Phe-Val-Arg-pNA and Bz-Phe-Val-Arg-pNA (Cortecs plc).

c. Protein Assay

Protein was measured using a DC protein assay kit supplied by Biorad. This is a modified method of Lowry et al., (1951. *Journal of Biological Chemistry.* 193: 265–275). Samples were compared to bovine serum albumin standards (0 to 1.5 mg/ml) prepared in either saline (0.9% w/v), 20 mM acetate buffer (pH 5.0) or 100 mM phosphate buffer (pH 6.0), as appropriate for the sample being analysed.

d. Preparation of Crude Bromelain

All the following steps were performed at ambient temperature (20 to 25° C.). A solution of crude bromelain (30 mg/ml) was prepared by dissolving 450 mg of powder in 15 ml of 20 mM acetate buffer (pH 5.0) containing 1 mM EDTA (disodium). The solution was centrifuged at 13,000×g for 15 minutes to remove insoluble material. The clear supernatant was used for chromatography.

e. SP Sepharose HP Cation Chromatography

An SP Sepharose HP column was prepared by packing 25 ml of media into an XK 16/20 column (Pharmacia Biotech) and equilibrated with 20 mM acetate buffer (pH 5.0) containing 1 mM EDTA (disodium), on a Perseptive Biosystems Workstation at 3 ml/min. 5 ml of crude bromelain solution (30 mg/ml) was injected onto the column and protein not bound to the column was collected. The column was then washed with 50 ml of acetate buffer and bound proteins were eluted with a linear gradient of 0 to 1.0 M NaCl in acetate buffer over 250 ml. 5 ml fractions were collected throughout the gradient. The fractions containing the CCX peak were pooled from 30 successive runs and analysed for protein, proteolytic activity, SDS-PAGE and isoelectric focusing.

f. Q Sepharose FF Anion Exchange Chromatography

Pooled CCX fractions obtained by cation chromatography were concentrated and buffer exchanged into 50 mM Tris/HCl (pH 8.5) by a combination of diafiltration, using a Filtron stirred cell (10 kDa molecular weight cut-off), and desalting using a Hitrap desalting column. Desalted CCX was then loaded onto 200 ml of Q Sepharose FF packed into an XK 50/20 column, equilibrated with Tris buffer at 12 ml/min, and attached to a Gradifrac Chromatography System (Pharmacia). The flow through, containing stem bromelain protease, was collected and the column washed with 10 column volumes of Tris buffer overnight. After washing the colurmn, CCX proteins adsorbed onto the column were eluted stepwise by the addition of 100 mM Phosphate buffer (pH 6.0) containing 4 M NaCl. The material eluted as a sharp main peak followed by additional material eluting slowly from the column as a 'tail' to the main peak. Two fractions were collected; one comprising of the main peak (and designated CCX2) and some 'tail' and the other containing only the 'tail' material (designated CCX1).

g. Phenyl Sepharose HP Hydrophobic Interaction Chromatography

The two CCX fractions obtained from Q Sepharose FF were subject to further purification by hydrophobic interaction chromatography (HIC). Briefly, 50 ml of Phenyl Sepharose HP was packed into an XK 26/20 column (attached to a Gradifrac chromatography system) and equilibrated with 100 mM phosphate buffer (pH 6.0) containing 4 M NaCl at 15 ml/min. The main CCX peak (CCX 2) and tail (CCX 1) from the anion exchange chromatography step were loaded and run separately on the Phenyl Sepharose column. Unbound protein in the flow through was collected and bound proteins were eluted with a decreasing linear salt gradient of 4 M to 0 M NaCl in phosphate buffer over ten column volumes (500 ml). This was followed by a stepwise change to 100% deionised water. 5 ml fractions were collected throughout the gradient and material eluting at the end of the gradient were pooled. The anion tail CCX 1 peak was collected as three fractions for analysis. CCX 2 protein and a '17 kDa protein' eluting from the column were separately pooled for analysis.

h. Processing of CCX for in vivo Testing

Samples of CCX obtained from cation chromatography, stem bromelain protease obtained from anion exchange and, CCX1, CCX2 and '17 kDa protein' obtained from HIC were concentrated by ultrafiltration in stirred cells (Filtron) containing a 10 kDa molecular weight cut-off membrane. After concentration, samples were buffer exchanged into sterile saline (0.9% w/v) containing Triton X-100 (0.001% v/v, reduced, carbonyl, peroxide free) by use of PD10 columns and then sterile filtered. Aliquots were retained for analysis and samples were sent to Dr Lloyd Kelland, at The Institute of Cancer Research, for assessment of anticancer activity in vivo as outlined in Example 7.

i. Sodium Dodecyl Sulphate Polyacrylamide Gel Electrophoresis

CCX samples were analysed under reducing conditions by sodium dodecyl sulphate polyacrylamide gel electrophoresis (SDS-PAGE) on precast Novex NuPAGE Bis Tris 4–12% T gradient gels, using an Xcell II Mini-Cell (Novex). Samples were prepared for electrophoresis by acid precipitation in which sample was mixed with an equal volume of 20% w/v trichloroacetic acid (TCA). The sample volume varied according to the protein concentration. Precipitated protein was collected by centrifugation at 13,000×g for 10 minutes and the supernatant discarded. The pellet was washed twice with 0.5 ml of diethyl ether and left to dry in air at ambient temperature. The pellets were then dissolved in Novex SDS-PAGE sample buffer and heated at 70° C. for 10 min. 20 µl samples were loaded onto the gel and electrophoresis was performed according to the manufacturers procedure (Novex) at constant voltage (200 V) until the dye front had reached the bottom of the gel (approximately 40 min). SDS-PAGE broad range molecular weight standards (BioRad) were diluted 1:400 in SDS-PAGE sample buffer, heated at 70° C. for 10 min, and electrophoresed concurrently with the samples. After electrophoresis, proteins were stained by use of the Gelcode blue colloidal coommassie stain reagent (Pierce Chemical Co).

j. Isoelectric Focusing

CCX samples were subjected to isoelectric focusing (IEF) on Ampholine PAGplate (pH 3.5–9.0) using a Pharmacia Multiphor II electrophoresis system, according to the manufacturer's instructions. IEF samples were first dialysed for 45 min by dispensing 50 µl onto a Millipore 0.025 µm membrane floated on 30 ml of deionised water. Briefly, 10 µl or 20 µl of sample or broad pI markers (Pharmacia) were loaded onto the gel and IEF was performed at 1500 V for 1.5 h. After electrophoresis, the proteins were fixed with a solution of TCA (20% w/v) for 20 min followed by two washes in deionised water of 15 min each to remove TCA. Proteins were stained for 1 h with Gelcode colloidal coomassie stain and destained overnight in deionised water.

k. Western Blotting

Pooled cation CCX was subjected to SDS-PAGE and Western blotted onto PVDF membrane. The membrane was stained with coomassie blue R-250 (0.025% w/v) dissolved in methanol (40% v/v) for 10 min, followed by destaining in methanol (50% v/v). The membrane was air dried at room temperature and stained proteins were sent for $NH_2$-terminal amino acid sequencing by Dr Mark Wilkinson, Department of Biochemistry at Liverpool University. Briefly, the protein bands on the membrane were excised and placed in the upper cartridge of the sequencer. NH$_2$-terminal amino acid analysis of CCX protein was determined by Edman degradation using a gas phase sequencer (Applied Biosystems), equipped with an on-line phenylthiohydantion amino acid analyser.

l. Peptide Mapping and NH$_2$-terminal Amino Acid Analysis of CCX

Cation and anion CCX (CCX2) were reduced, carboxymethylated and digested with trypsin. The resulting digest was subject to peptide mapping by HPLC on a narrow bore C$_{18}$ column by Dr. Mark Wilkinson, Liverpool University. The peptides were eluted from the column by a linear gradient of 0 to 65% acetonitrile, containing trifluoroacetic acid (0.1% v/v), over 40 min. The main peptides eluting from the column were collected and subject to NH$_2$-terminal sequencing.

Results a. Purification of CCX

Figure 12:
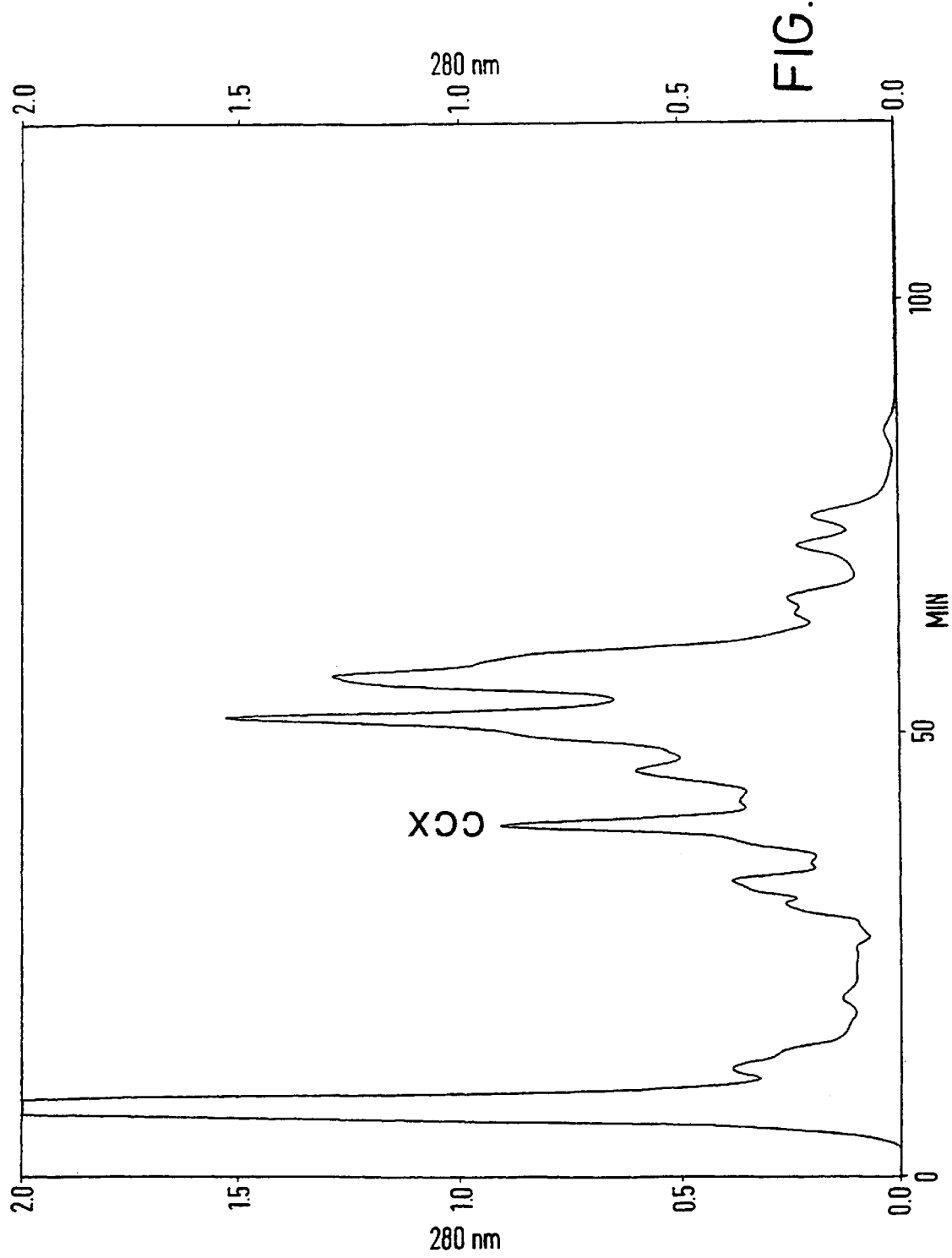
FIG. 12 shows the ultraviolet trace of the cation exchange chromatography of crude bromelain using SP Sepharose HP media. The column containing 25 ml of media was equilibrated with 20 mM acetate buffer (pH 5.0) containing 1 mM EDTA at 3 ml/min. Proteins were eluted on a 10 column volume linear gradient of 0 to 1.0 M NaCl in acetate buffer. 5 ml fractions were collected throughout the gradient and the CCX fraction indicated on the trace was pooled from 30 runs.
Figure 13:
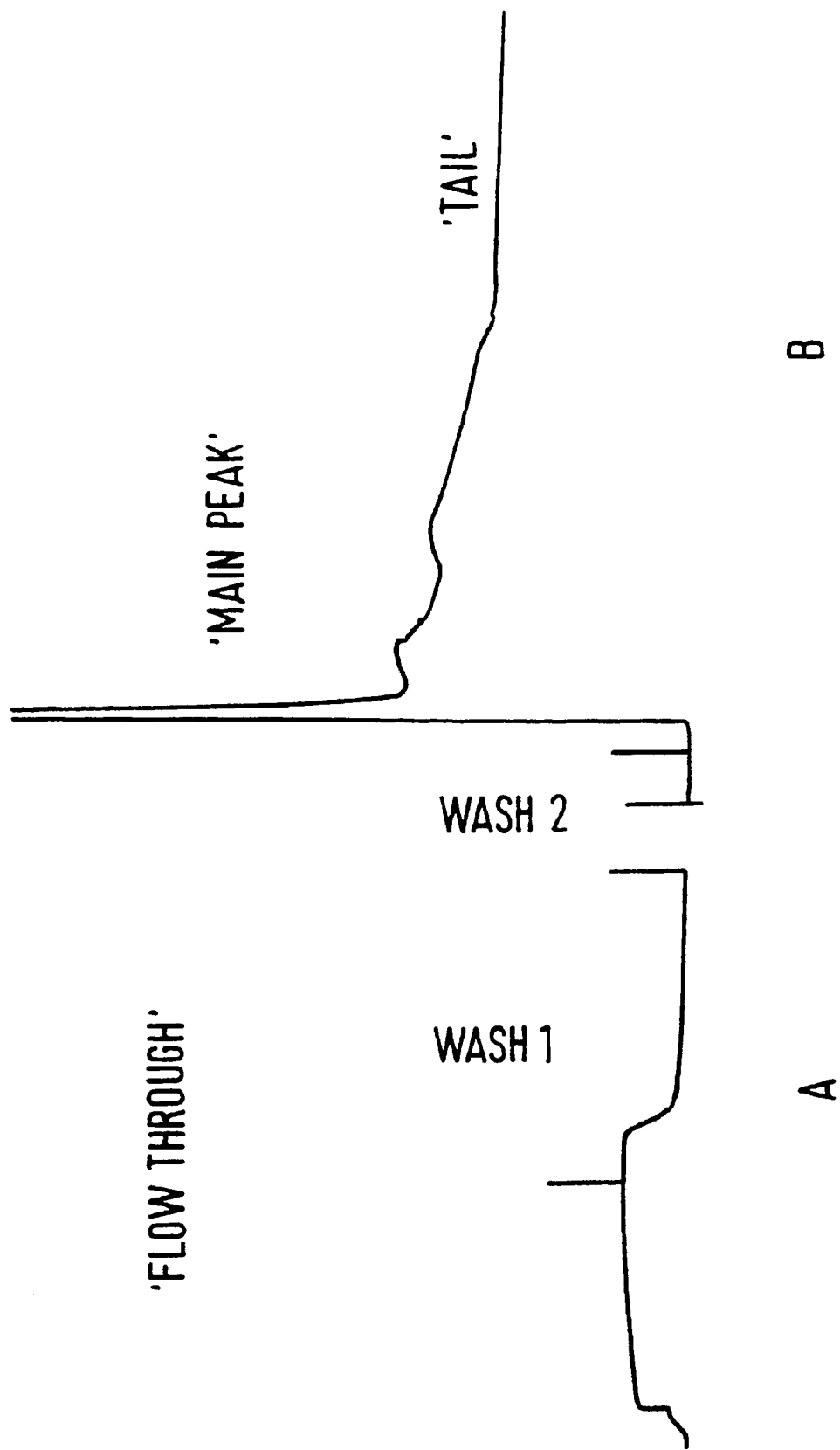
FIG. 13 shows the ultraviolet trace of the anion exchange chromatography of CCX (obtained from cation exchange chromatography) using Q Sepharose FF. Pooled and desalted fraction CCX was applied to 200 ml of media packed into an XK 50/20 column at a flow rate of 12 ml/min. Part A of the U.V. trace shows contaminating stem bromelain protease eluting in the flow-through fraction. Cation CCX was eluted by a stepwise change to phosphate buffer containing 4 M NaCl. Part B of the trace shows a rapidly eluting peak of protein followed by slower eluting protein tailing from the column. The flow-through, initial peak and tail were collected separately for analysis and processing.

FIG. 12 shows a typical U.V. chromatogram of crude stem bromelain run on SP Sepharose High Performance media. Samples containing the indicated CCX fraction were pooled from 30 runs. To remove contaminating stem bromelain protease, the cation CCX was desalted into Tris/HCl buffer (pH 8.5), by use of a desalting column, and adsorbed onto Q Sepharose HP. Due to differences in the pI of stem bromelain protease and CCX protease, we predicted that the major CCX proteins should adsorb onto the column, and contaminating stem bromelain elute in the column flow-through. FIG. 13A shows the U.V trace of Q Sepharose column and confirms that contaminating stem bromelain is collected in the flow-through. The main CCX proteins were eluted stepwise in phosphate buffer containing 4 M NaCl. FIG. 13B shows that the protein did not elute as a sharp peak but, after an initial rapid rise and fall, has a significant tail due to protein eluting more slowly from the column. This indicates a difference in the behaviour of proteins in the CCX fraction. The tailing of protein is probably due to non-specific hydrophobic interaction with the chromatographic matrix (Sepharose). The protein eluting from the column was collected in two fractions; one containing the material eluting first and containing some of the tail protein (CCX2), and one containing only the tail protein (CCX1).

Figure 14:
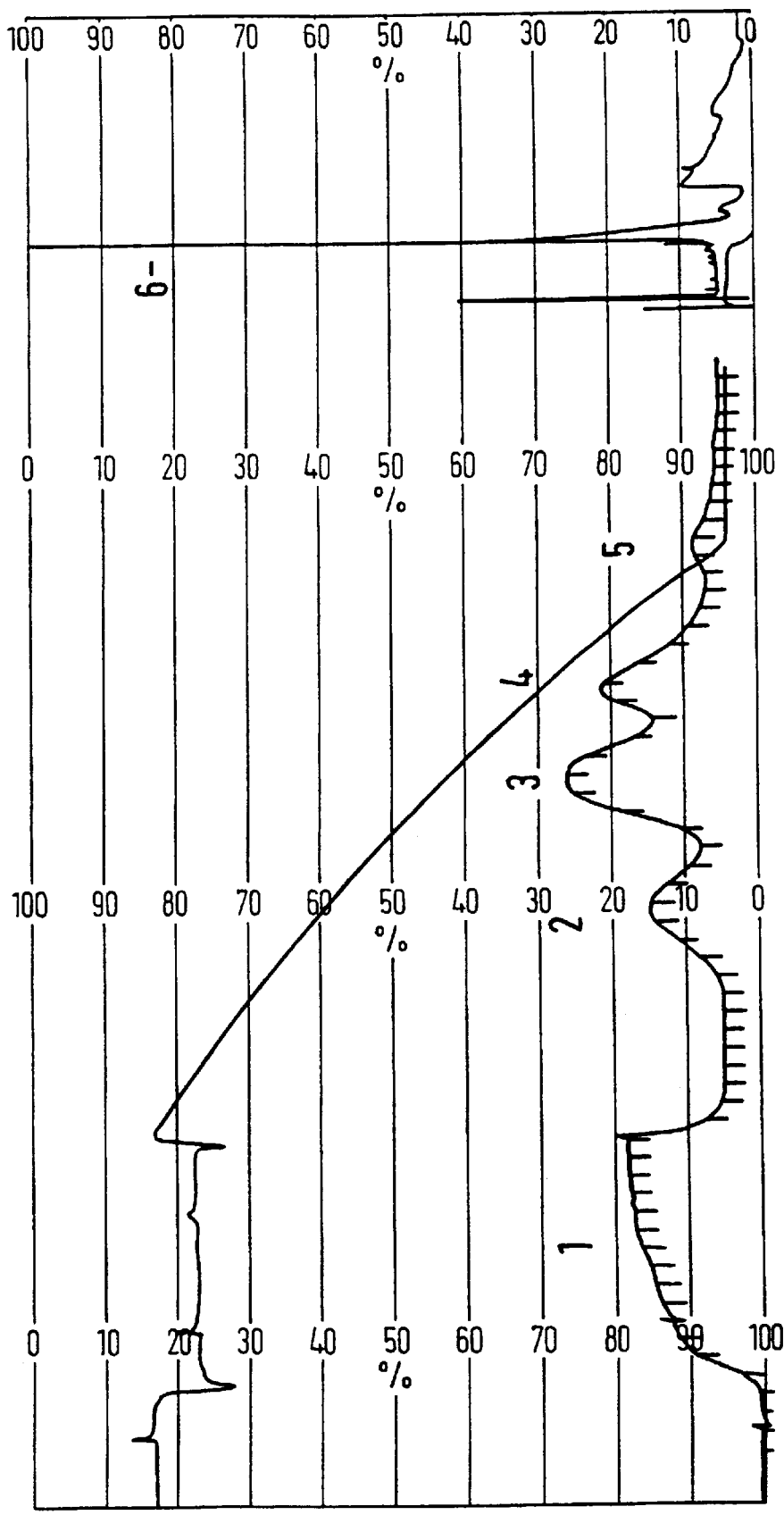
FIG. 14 shows the hydrophobic interaction chromatography of CCX "Main Peak" (obtained from anion exchange chromatography) using Phenyl Sepharose HP Media. 50 ml of media was packed into an XK 26/20 column. Anion CCX was applied to the column which was then equilibrated in 100 mM phosphate buffer containing 4 M NaCl at a flow rate of 15 ml/min. Proteins were eluted with a descending NaCl gradient to phosphate buffer (containing no NaCl), followed by a stepwise elution with deionised water. The main peak (shown here as peak 6) was pooled separately for analysis.
Figure 15:
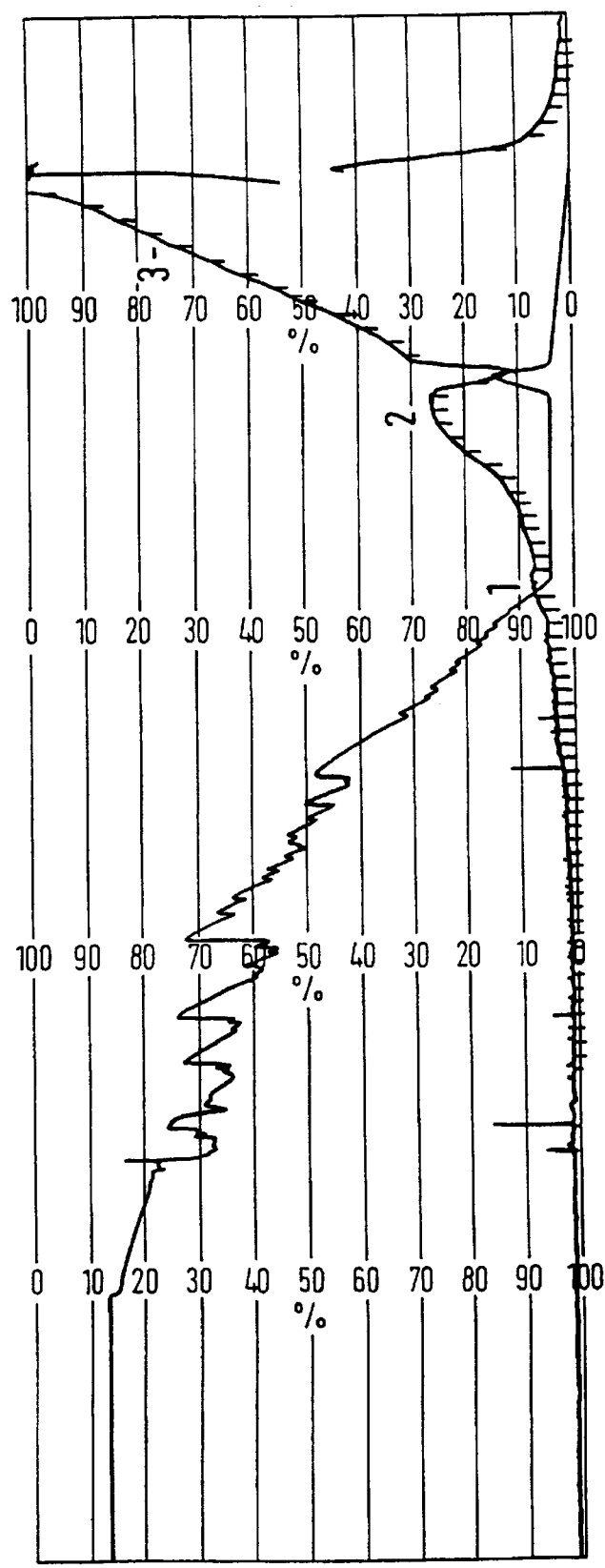
FIG. 15 shows the hydrophobic interaction chromatography of anion CCX "Tail" using Phenyl Sepharose HP Media 50 ml of media was packed into an XK 26/20 column. Anion CCX was applied to the column which was then equilibrated in 100 mM phosphate buffer containing 4 M NaCl. Proteins were eluted with a descending salt gradient to phosphate buffer (containing no NaCl) followed by a stepwise elution with deionised water. The main peak eluting on stepwise change to deionised water was collected as 3 separate fractions (shown here as peak 1 to 3) for analysis and processing.

The two anion fractions were subject to HIC on Phenyl Sepharose HP media. FIG. 14 shows the elution profile of CCX2 from the HIC column. Some proteins elute in the flow-through and others on the gradient (peaks 1 to 5), but the major protein elutes at the end of the gradient after switching to 100% water (peak 6). The flow-through and peak 1 contain a protein of approximately 17 kDa in size. When CCX1 is run on the HIC column, a different elution profile emerges (FIG. 15). There is no protein contained within the flow-through and no proteins elute on the salt gradient; the main protein elutes at the end of the gradient and after stepping to 100% water.

b. SDS PAGE

Figure 16:
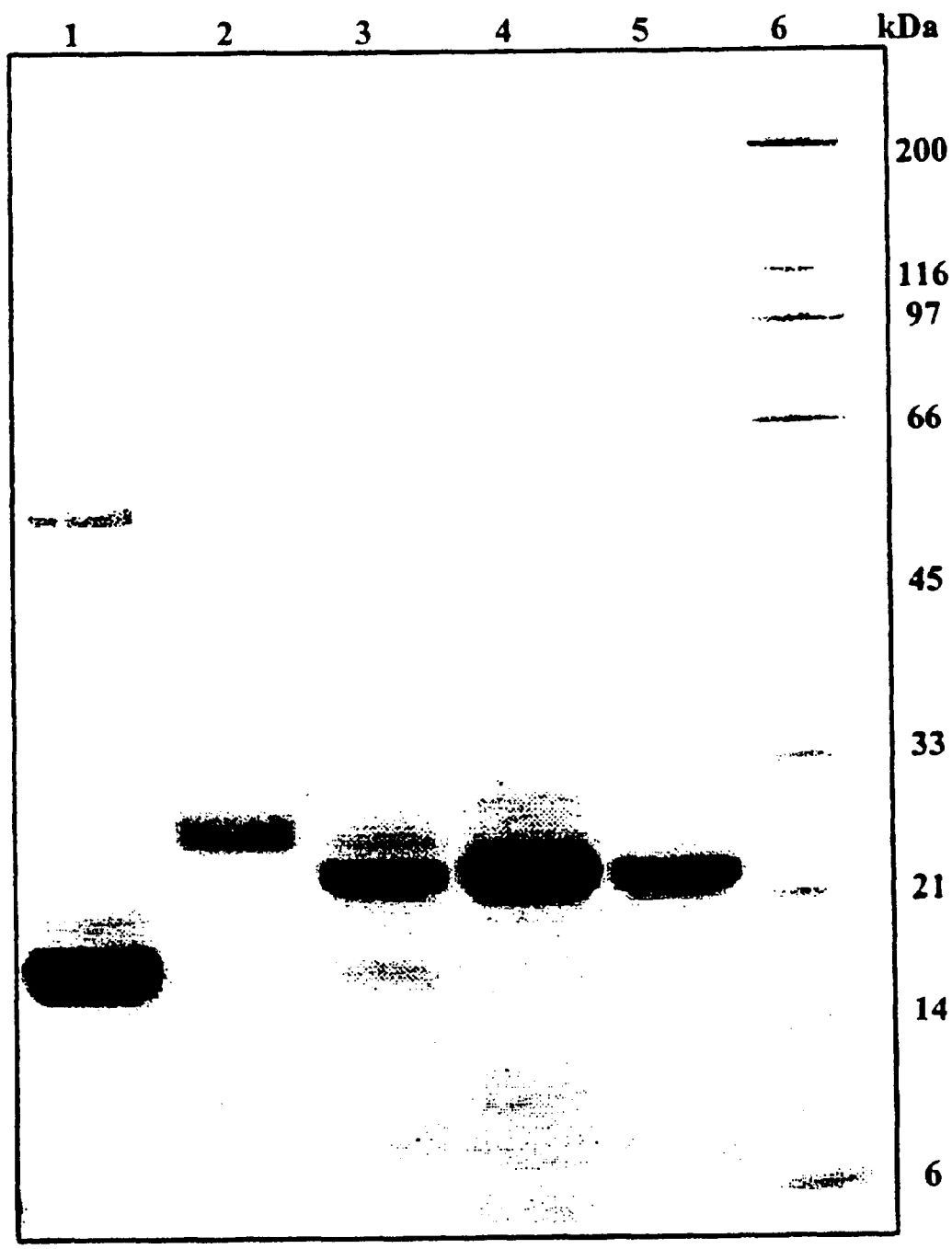
FIG. 16 shows the SDS-PAGE of purified CCX proteins. Samples were run on Novex 4–12% T Mini-Gels. Column 1, HIC purified '17 kDa protein' (from anion main peak); 2, stem bromelain protease from anion flow-through; 3, CCX from cation chromatography; 4, HIC purified CCX2 protease; HIC purified CCX1 protease; 6, Molecular weight markers.

FIG. 16 shows the SDS-PAGE analysis of CCX samples used for in vivo testing in Example 7. Cation CCX (lane 3) shows a main protein present at 22.1 kDa, but there are a number of minor contaminants present at 24.9 kDa and 16.6 kDa similar to those described previously in Example 1. The minor 76 kDa protein described previously in Example 1 does not appear to be present in the current preparation. The stem bromelain protease flow-through from the anion column clearly shows this to be of a different molecular weight to the main CCX protein and is present as a single 25 kDa major band (lane 2). CCX2 and CCX1 obtained from the HIC column are shown in lanes 4 and 5, respectively. CCX2 shows a main 22.2 kDa band with some minor lower and higher molecular weight contaminants present in the preparation. CCX1 is present as a single 22.2 kDa band. The protein labelled as '17 kDa' reveals a main 16.2 kDa band and some minor contaminants at 19, 35, and 51 kDa.

c. Isoelectric Focusing

Figure 17:
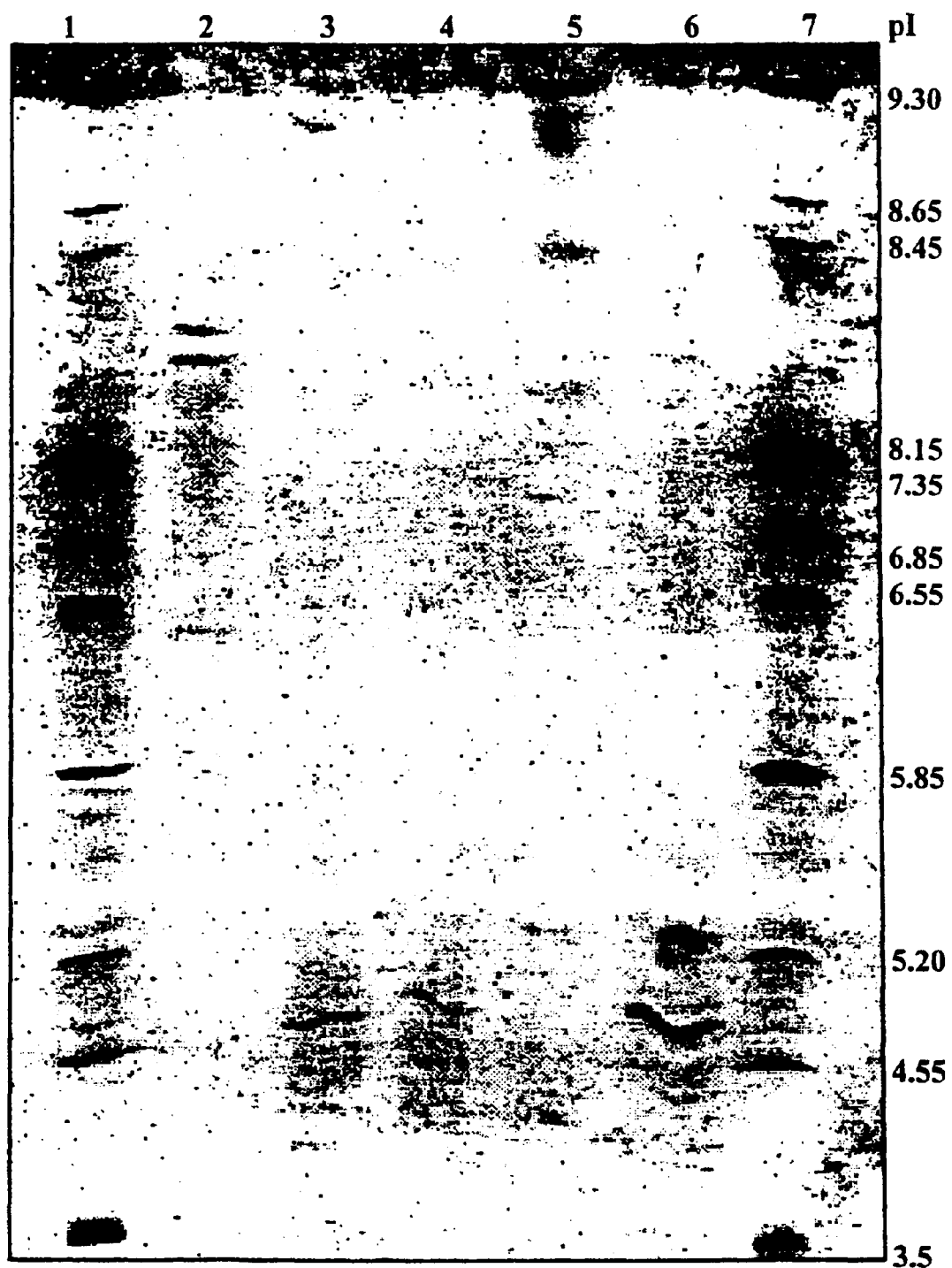
FIG. 17 shows the isoelectric focusing of purified CCX proteins. Samples were run on Ampholine PAGplates (pH 3.5 to 9.0). Column 1, pI markers; 2, HIC purified "17 kDa protein"; 3, HIC purified CCX1 protease (from anion "tail fraction"); 4, HIC purified CCX2 protease (from anion main peak); 5, anion purified stem bromelain protease; 6, fraction CCX from cation chromatography; 7, pI markers.

FIG. 17 shows the IEF of CCX samples used in in vivo tests described in Example 7. Cation CCX shows two main protein bands focusing at pI's of 4.67 and 4.79. Minor contaminants are also present in the pI range of 4.3 to 4.4. The stem bromelain protease flow-through obtained from the cation flow-through focuses at the basic end (extrapolated pI=9.3) as expected. CCX2 and CCX1 obtained from the HIC column show one main protein band focusing at pI 4.79 and pI 4.67 respectively. The IEF suggests the existence of two closely related proteinases in the cation CCX preparation. The '17 kDa' protein has two bands focusing at pI's of 8.01 and 8.16; a minor contaminant is also present of pI 6.67.

d. Proteinase Assays

The results of proteolytic activity of CCX proteins during each stage of purification are shown in Table 5. Results are expressed as specific activities so that results can be compared directly for the various fractions. Z-Arg-Arg-pNA is a good substrate for stem bromelain, whereas Z-Phe-Val-Arg-pNA and Bz-Phe-Val-Arg-pNA are good substrates for the fruit bromelain proteinases. Cation CCX shows activity against both substrates but is most active against Z-Phe-Val-Arg-pNA. Stem bromelian protease from the cation flow-through has a high specific activity towards Z-Arg-Arg-pNA but lower activity towards Z-Phe-Val-Arg-pNA. The CCX main peak and CCX tail, from the cation column, display different specific activities towards Z-Phe-Val-Arg-pNA, but have low activity towards Z-Arg-Arg-pNA. After HIC, the purified CCX2 and CCX1 also show differences in their specific activity against Z-Phe-Val-Arg-pNA; both have virtually no activity against Z-Arg-Arg-pNA. CCX2 and CCX1 processed for in vivo testing also show differences in their specific activities against Bz-Phe-Val-Arg-pNA. The data confirm that stem bromelain protease is originally present in cation exchange preparations of CCX and that further procedures designed to obtain pure CCX2, successfully remove the contaminating stem bromelain protease. The differences in the specific activities of CCX2 and CCX1 suggest that these enzymes have different substrate specificities.

e. NH$_2$ Amino Acid Analysis

Table 6 shows the internal peptide sequences derived from Western blotting, and peptide mapping of cation and anion CCX. These sequence was compared with protein sequences deposited on the DDBJ/EMBL/GenBank databases. CCX peptides show homology with stem bromelain protease but most closely match to sequences obtained from the fruit bromelains. However, none of the fruit and bromelain sequences 100% match CCX. This suggests that CCX is a different but closely related enzyme(s) to those deposited on the DDBJ/EMBL/GenBank databases.

Conclusion

CCX obtained by cation exchange chromatography has shown to contain one main protein of an estimated Mr of 22.2 kDa but also contains a number of other proteins. The purification scheme described has enabled the purification of four of these components in sufficient quantities for characterisation studies and testing in vitro and in vivo. The proteins have been identified as stem bromelain protease, a '17 kDa protein' and two CCX proteases, designated as CCX1 and CCX2. The CCX proteases fractionated by first cation chromatography, followed by anion and hydrophobic interaction chromatography, display differences in their specific activities against a number of synthetic peptide substrates; they also have different isoelectric points. NH$_2$-terminal amino acid sequences of internal peptides show that the CCX proteases isolated from the stem of the pineapple plant are closely related to fruit bromelain protease sequences derived from the fruit of the pineapple.

TABLE 5

The Specific Activities of CCX Proteins Against Synthetic Proteinase Substrates.

| Sample | Z-Arg-Arg-pNA (nmoles.min/mg protein) | Z-Phe-Val-Arg-pNA (nmoles.min/mg protein) | Bz-Phe-Val-Arg-pNA (nmoles.min/mg protein) |
|---|---|---|---|
| Anion CCX | | | |
| Flow-through | 638 | 95 | nd |
| Main Peak | nd | nd | nd |
| Tail | nd | nd | nd |
| HIC CCX2 | | | |
| Peak 1 | nd | nd | nd |
| Peak 2 | 29 | 3 | nd |
| Peak 3 | 37 | 2 | nd |
| Peak 4 | 54 | 3 | nd |
| Peak 5 | 484 | 134 | nd |
| Peak 6 | 6 | 552 | nd |
| HIC CCX1 | | | |
| Peak 1 | nd | nd | nd |
| Peak 2 | 25 | 1090 | nd |
| Peak 3 | 1 | 225 | nd |
| Samples tested in vivo | | | |
| Cation CCX | nd | nd | 598.5 |
| Anion Stem Bromelain | nd | nd | 95.5 |
| '17 kDa' | nd | nd | 21.3 |
| CCX2 (Peak 5) | nd | nd | 706.8 |
| CCX1 (Peak 3) | nd | nd | 51.3 |

Example 7

Anti-Tumour Efficacy of Purified CCX Protein Against the CH1 Human Ovarian Carcinoma Xenograft in vivo To confirm that the purified CCX protein was indeed the active anti-tumour component in fraction CCX and not any recognised contaminant, we tested the components separated in Example 6 for anti-tumour activity in animal models in vivo. Again, in vivo studies were conducted by Dr Lloyd Kelland, CRC Centre for Cancer Therapeutics at The Institute of Cancer Research.

a. CCX

CCX1, CCX2, and the 17 kda protein contaminant were supplied at a concentration of 1.25 mg/ml, 0.97 mg/ml and 1.22 mg/ml dissolved in 0.9% saline, respectively. Stem bromelain protease was supplied at a concentration of 0.66 mg/ml. Samples were provided on ice and the first injection was administered immediately upon receipt of samples. The remaining material was stored at −20° C. until required.

b. CH1 Human Ovarian Carcinoma Xenograft

Female nude (nu/nu) mice aged 6 to 8 weeks were used for the study and maintained as previously described in Example 3. When tumours had reached an average maximum diameter of 6 to 8 mm, mice were randomised to receive either CCX1 (12.5 mg/kg), CCX2 (12.5 mg/kg), stem bromelain protease (4 mg/kg) or 17 kda protein (12.5 mg/kg) administered intravenously into the tail vein (n=5 animals per treatment). Five animals were randomised to receive saline alone (controls). Treatments were administered on days 0, 4 and 8 following randomisation of animals and approximately 6 weeks after tumours were implanted.

c. Evaluation of Efficacy of CCX

Mice were monitored daily for signs of drug or tumour-induced stress/toxicity as described in Example 3. Tumour diameters were measured twice weekly using slide callipers and Tumour Volumes were determined as described in Example 3. Antitumour effects were assessed in terms of the ratio of mean tumour volume of treated versus control groups. In addition, growth delays (the difference in days for treated versus control tumours to double in volume) were calculated.

To assess drug-induced toxicity, mice body weights were recorded twice weekly and, at the termination of the experiment, major organ histology was conducted.

d. Statistics

The significance of differences between each treated and control group was assessed using a Student's t-test (independent, two tailed). $P<0.05$ was regarded as significant.

Results

Figure 18:
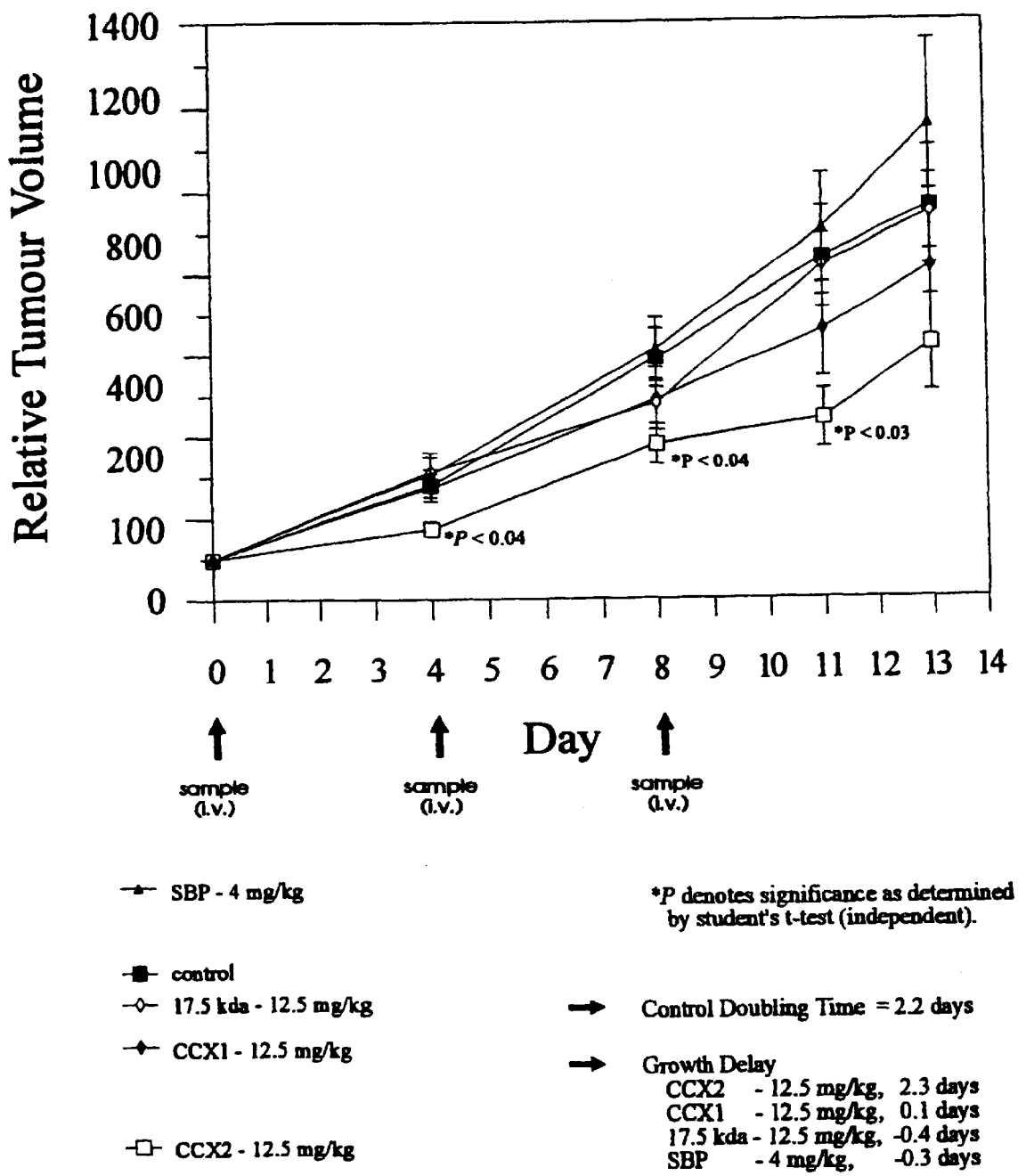
FIG. 18 shows the growth inhibitory activity of purified CCX1, CCX2, stem bromelain protease (SBP) and the "17 kDa protein" against human ovarian tumours implanted in nude mice. Arrows indicate the day the samples were administered. Day 0 is approximately 4 weeks after tumours were implanted.

FIG. 18 shows that CCX2, but not CCX1 exhibits clear evidence of in vivo anti-tumour activity against the CH1 human ovarian carcinoma. The minor contaminants contained within fraction CCX, such as stem bromelain protease and the 17 kda protein did not display any anti-tumour activity.

At day 8, a tumour reduction of 36% ($p<0.04$) was observed in the CCX2 treatment group compared to untreated controls. By day 11, a 47% ($p<0.03$) reduction in tumour size was observed. The statistically significant reduction in tumour growth was observed in the absence of any CCX2-induced toxicity. Similarly to the results in Example 3, there was no significant reduction in animal body weight.

Data from this study confirm that the active component within the fraction CCX mixture is indeed, a major protein termed CCX2. It is not clear why CCX1, a very closely related enzyme, has no has no effect on tumour growth. Currently CCX1 and CCX2 are not distinguishable by cation exchange chromatography, but are distinguishable by their different elution profile from an anion exchange column and differences in specific enzyme activity (Example 6). This data suggests that CCX2 has a very specific mode of action.

TABLE I

Peptide sequences of novel protein (CCX) derived from bromelain.

| Peptide | Amino Acid (single letter code) | | | | | | | | | | | | | | | | | |
|---|---|---|---|---|---|---|---|---|---|---|---|---|---|---|---|---|---|---|
| NH2-term | V | P | Q | S | I | D | W | R | D | Y | G | A | V | N | E | V | K | N |
| SEQ ID NO:1 | Val | Pro | Gln | Ser | Ile | Asp | Trp | Arg | Asp | Tyr | Gly | Ala | Val | Asn | Glu | Val | Lys | Asn |
| SEQ ID NO:2 | G | G | W | E | F | K | | | | | | | | | | | | |
| | Gly | Gly | Trp | Glu | Phe | Lys | | | | | | | | | | | | |
| SEQ ID NO:3 | K | A | V | N | G | | | | | | | | | | | | | |
| | Lys | Ala | Val | Asn | Gly | | | | | | | | | | | | | |
| SEQ ID NO:4 | Y | W | I | V | R | | | | | | | | | | | | | |
| | Tyr | Trp | Ile | Val | Arg | | | | | | | | | | | | | |

TABLE I-continued

Peptide sequences of novel protein (CCX) derived from bromelain.

| Peptide | Amino Acid (single letter code) | | | | | | | | | | | | | | |
|---|---|---|---|---|---|---|---|---|---|---|---|---|---|---|---|
| SEQ ID NO:5 | N | S | W | G | S | S | W | G | E | G | G | Y | V | R | |
| | Asn | Ser | Trp | Gly | Ser | Ser | Trp | Gly | Glu | Gly | Gly | Tyr | Val | Arg | |
| SEQ ID NO:6 | T | S | L | N | H | A | I | T | I | I | V | Y | | | |
| | Thr | Ser | Leu | Asn | His | Ala | Ile | Thr | Ile | Ile | Val | Tyr | | | |
| SEQ ID NO:7 | L | P | E | F Q | P Q | V | L | D | — | A | — | | | | |
| | Leu | Pro | Glu | Phe Gln | Pro Gln | Val | Leu | Asp | | Ala | | | | | |
| SEQ ID NO:8 | G | V | S | S | S | S | G | A | C | G | I | A | M | S | P | L | — | T | — |
| | Gly | Val | Ser | Ser | Ser | Ser | Gly | Ala | Cys | Gly | Ile | Ala | Met | Ser | Pro | Leu | | Thr | |
| SEQ ID NO:9 | G | G | V | F | S | G | P | A | G | | | | | | |
| | Gly | Gly | Val | Phe | Ser | Gly | Pro | Ala | Gly | | | | | | |
| SEQ ID NO:10 | N | N | A | Y | | | | | | | | | | | |
| | Asn | Asn | Ala | Tyr | | | | | | | | | | | |
| SEQ ID NO:11 | S | S | G | T | K | Y | W | — | V | — | | | | | |
| | Ser | Ser | Gly | Thr | Lys | Tyr | Trp | | Val | | | | | | |

What is claimed is:

1. A protein which is a component of stem bromelain, has a molecular weight of about 25.08 kDa as determined by SDS-PAGE, has an isoelectric point of about 3.8 or 3.85 and has the amino terminal sequence:

Val Pro Gln Ser Ile Asp Trp Arg Asp Tyr Gly Ala Val Asn Glu Val Lys Asn (SEQ ID NO:1)

and, additionally, contains the following sequences:

Gly Gly Trp Glu Phe Lys (SEQ ID NO:2)

Lys Ala Val Asn Gly (SEQ ID NO:3)

Tyr Trp Ile Val Arg (SEQ ID NO:4)

Asn Ser Trp Gly Ser Ser Trp Gly Glu Gly Gly Tyr Val Arg (SEQ ID NO:5)

Thr Ser Leu Asn His Ala Ile Thr Ile Ile Val Tyr (SEQ ID NO:6)

Leu Pro Glu Phe (Gln) Pro (Gln) Val Leu Asp-Ala- (SEQ ID NO:7)

Gly Val Ser Ser Ser Ser Gly Ala Cys Gly Ile Ala Met Ser Pro Leu-Thr- (SEQ ID NO:8)

Gly Gly Val Phe Ser Gly Pro Ala Gly (SEQ ID NO:9)

Asn Asn Ala Tyr (SEQ ID NO: 10)

Ser Ser Gly Thr Lys Tyr Trp-Val- (SEQ ID NO:11);

where the bracketed amino acids represent alternatives to the preceding amino acid and a "-" represents an unidentified amino acid.

2. A protein which is a component of stem bromelain, has a molecular weight of about 25.08 kDa as determined by SDS-PAGE, has an isoelectric point of 3.8 or 3.85, and is obtainable by the following method:

(a) dissolving bromelain in 20 mM acetate buffer at pH 5.0 containing 1 mM disodium EDTA;

(b) separating the components of bromelain by fast protein liquid chromatography on SP-sepharose HP, eluting with a linear gradient of 0 to 1.0 M sodium chloride in acetate buffer over 250 ml;

(c) collecting the fraction corresponding to the second sharp peak off the column, concentrating and exchanging into 50 mM Tris/HCl buffer (pH 8.5) and desalting this fraction;

(d) separating the components of the fraction from step (c) by anion exchange chromatography on Q sepharose packed into an XK 50/20 column, equilibrating with Tris buffer and eluting with 100 mM phosphate buffer (pH 6.0) to give a main peak (designated CCX2) and tail material (designated CCX1); and (e) further purifying the CCX2 material using hydrophobic interaction chromatography on phenyl sepharose HP in an XK 26/20 column, equilibrating with 100 mM phosphate buffer (pH 6.0) and eluting with a decreasing linear salt gradient of 4 M to 0 M NaCl in phosphate buffer over ten column volumes followed by a stepwise change to 100% deionised water and collecting the CCX2 fraction.

3. A pharmaceutical or veterinary composition comprising a protein as claimed in claim 1 or claim 2 together with a pharmaceutically or veterinarily acceptable excipient.

4. A composition as claimed in claim 3, wherein said composition formulated for enteral administration.

5. The composition of claim 4, wherein said composition is formulated for oral, nasal, buccal, topical or anal administration.

6. A composition as claimed in claim 3, wherein said composition is formulated for parenteral administration.

7. The composition of claim 6, wherein said composition is formulated for intravenous, subcutaneous, intramuscular or intraperitoneal administration.

* * * * *

SEQUENCE LISTING

<160> NUMBER OF SEQ ID NOS: 11

<210> SEQ ID NO 1
<211> LENGTH: 18
<212> TYPE: PRT
<213> ORGANISM: Ananas comosus

<400> SEQUENCE: 1

Val Pro Gln Ser Ile Asp Trp Arg Asp Tyr Gly Ala Val Asn Glu
 1               5                  10                  15

Val Lys Asn

<210> SEQ ID NO 2
<211> LENGTH: 6
<212> TYPE: PRT
<213> ORGANISM: Ananas comosus

<400> SEQUENCE: 2

Gly Gly Trp Glu Phe Lys
 1               5

<210> SEQ ID NO 3
<211> LENGTH: 5
<212> TYPE: PRT
<213> ORGANISM: Ananas comosus

<400> SEQUENCE: 3

Lys Ala Val Asn Gly
 1               5

<210> SEQ ID NO 4
<211> LENGTH: 5
<212> TYPE: PRT
<213> ORGANISM: Ananas comosus

<400> SEQUENCE: 4

Tyr Trp Ile Val Arg
 1               5

<210> SEQ ID NO 5
<211> LENGTH: 14

```
<212> TYPE: PRT
<213> ORGANISM: Ananas comosus

<400> SEQUENCE: 5

Asn Ser Trp Gly Ser Ser Trp Gly Glu Gly Gly Tyr Val Arg
  1               5                  10

<210> SEQ ID NO 6
<211> LENGTH: 12
<212> TYPE: PRT
<213> ORGANISM: Ananas comosus

<400> SEQUENCE: 6

Thr Ser Leu Asn His Ala Ile Thr Ile Ile Val Tyr
  1               5                  10

<210> SEQ ID NO 7
<211> LENGTH: 11
<212> TYPE: PRT
<213> ORGANISM: Ananas comosus
<220> FEATURE:
<221> NAME/KEY: Modified site
<222> LOCATION: 4..5; 9; 11
<223> OTHER INFORMATION: "Amino acid no. 4 is either Phe or Gln; Amino
      acid no.5 is either Pro or Gln; Amino acid nos. 9 and 11 are
      unidentified amino acids"

<400> SEQUENCE: 7

Leu Pro Glu Xaa Xaa Val Leu Asp Xaa Ala Xaa
  1               5                  10

<210> SEQ ID NO 8
<211> LENGTH: 19
<212> TYPE: PRT
<213> ORGANISM: Ananas comosus
<220> FEATURE:
<221> NAME/KEY: Modified site
<222> LOCATION: 17; 19
<223> OTHER INFORMATION: "Amino acid nos. 17 and 19 are unidentified
      amino acids"

<400> SEQUENCE: 8

Gly Val Ser Ser Ser Ser Gly Ala Cys Gly Ile Ala Met Ser Pro
  1               5                  10                  15

Leu Xaa Thr Xaa

<210> SEQ ID NO 9
<211> LENGTH: 9
<212> TYPE: PRT
<213> ORGANISM: Ananas comosus

<400> SEQUENCE: 9

Gly Gly Val Phe Ser Gly Pro Ala Gly
  1               5

<210> SEQ ID NO 10
<211> LENGTH: 4
<212> TYPE: PRT
<213> ORGANISM: Ananas comosus

<400> SEQUENCE: 10

Asn Asn Ala Tyr
  1

<210> SEQ ID NO 11
<211> LENGTH: 10
```

```
-continued

<212> TYPE: PRT
<213> ORGANISM: Ananas comosus
<220> FEATURE:
<221> NAME/KEY: Modified site
<222> LOCATION: 8, 10
<223> OTHER INFORMATION: "Amino acid nos. 8 and 10 are unidentified
      amino acids"

<400> SEQUENCE: 11

Ser Ser Gly Thr Lys Tyr Trp Xaa Val Xaa
1               5                   10
```